(12) United States Patent
Robinson

(10) Patent No.: US 9,717,540 B2
(45) Date of Patent: Aug. 1, 2017

(54) INTER-SPINOUS PROCESS DEVICE AND METHOD

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days.

(21) Appl. No.: 14/507,915

(22) Filed: Oct. 7, 2014

(65) Prior Publication Data

US 2015/0025583 A1  Jan. 22, 2015

Related U.S. Application Data

(62) Division of application No. 13/657,777, filed on Oct. 22, 2012, now Pat. No. 8,906,065.

(51) Int. Cl.
*A61B 17/70* (2006.01)
*A61B 17/88* (2006.01)

(52) U.S. Cl.
CPC ...... *A61B 17/7068* (2013.01); *A61B 17/7067* (2013.01); *A61B 17/88* (2013.01)

(58) Field of Classification Search
CPC .............. A61B 17/7068; A61B 17/88
See application file for complete search history.

(56) References Cited

U.S. PATENT DOCUMENTS

| | | | | |
|---|---|---|---|---|
| 7,048,736 B2* | 5/2006 | Robinson | ........... | A61B 17/7068 606/250 |
| 7,727,233 B2* | 6/2010 | Blackwell | .......... | A61B 17/7068 606/251 |
| 8,048,120 B1* | 11/2011 | Fallin | ................. | A61B 17/7068 606/246 |
| 8,123,782 B2* | 2/2012 | Altarac | .............. | A61B 17/7065 606/248 |
| 8,382,801 B2* | 2/2013 | Lamborne | .......... | A61B 17/7068 606/246 |
| 2007/0233082 A1* | 10/2007 | Chin | .................. | A61B 17/7065 606/276 |
| 2008/0183211 A1* | 7/2008 | Lamborne | .......... | A61B 17/7068 606/249 |
| 2011/0022090 A1* | 1/2011 | Gordon | .............. | A61B 17/7068 606/249 |
| 2011/0029020 A1* | 2/2011 | Gordon | .............. | A61B 17/7062 606/248 |
| 2011/0066186 A1* | 3/2011 | Boyer, II | ........... | A61B 17/7065 606/249 |
| 2011/0137348 A1* | 6/2011 | Jackson | ............... | A61B 17/701 606/264 |
| 2011/0319936 A1* | 12/2011 | Gordon | .............. | A61B 17/7068 606/248 |

(Continued)

*Primary Examiner* — Ellen C Hammond
(74) *Attorney, Agent, or Firm* — FisherBroyles, LLP; Anthony J. DoVale

(57) ABSTRACT

An implantable device and method for fixation of spinous processes is presented. The device has first and second spaced plates, the first plate having a surface facing a surface of the second plate. The plates are configured for placement on either side of two adjacent spinous processes. The plates are held in place adjacent each side of the two spinous processes by a post connected to each of the plates and extending substantially therefrom the facing surface of the first plate to at least the facing surface of the second plate.

16 Claims, 32 Drawing Sheets

(56) References Cited

U.S. PATENT DOCUMENTS

| | | | |
|---|---|---|---|
| 2012/0016418 A1* | 1/2012 | Chin | A61B 17/7068 606/249 |
| 2012/0150228 A1* | 6/2012 | Zappacosta | A61B 17/7068 606/248 |
| 2012/0226314 A1* | 9/2012 | Chin | A61L 27/425 606/249 |
| 2012/0265204 A1* | 10/2012 | Schmierer | A61B 17/1671 606/70 |

* cited by examiner

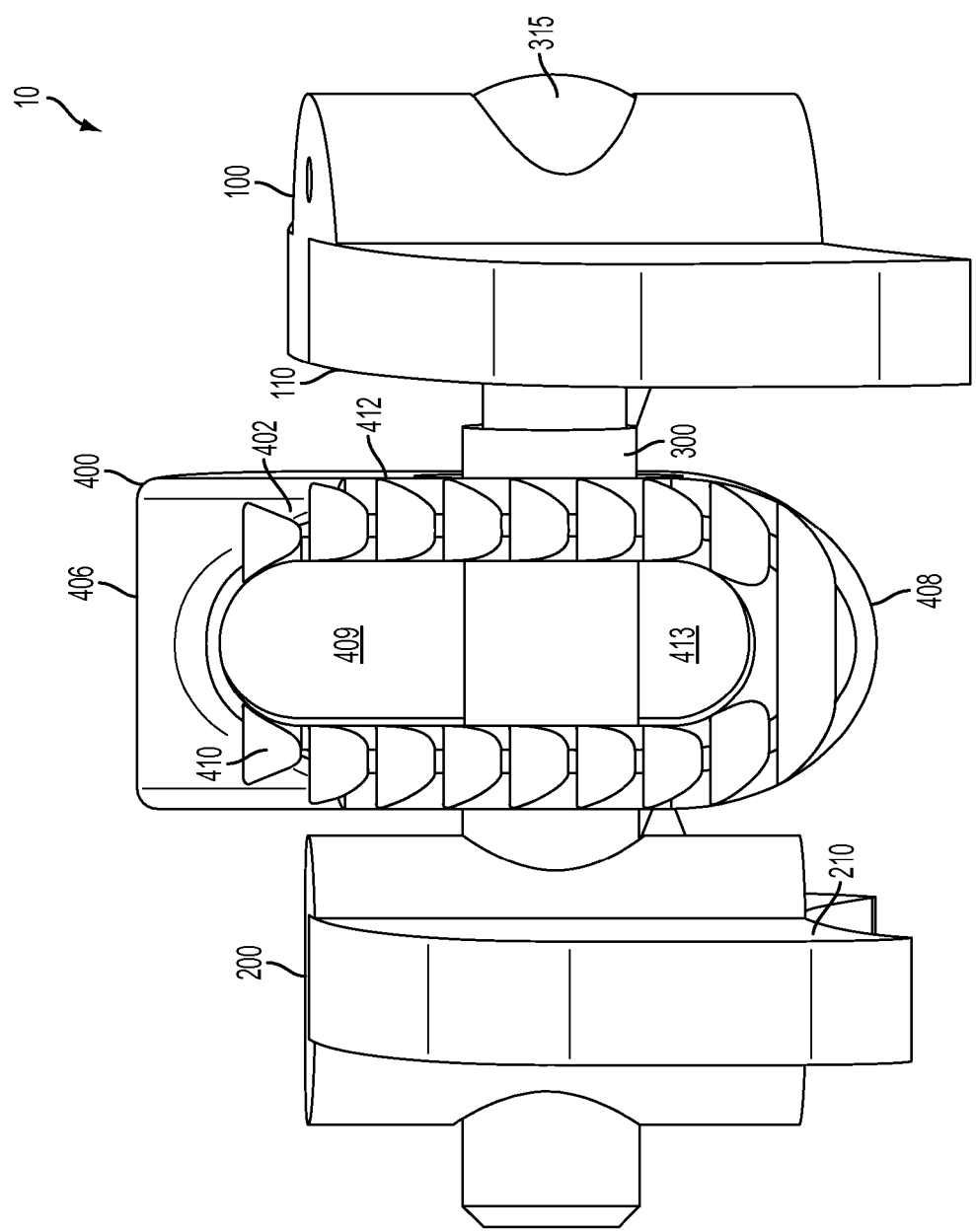

INTER-SPINOUS PROCESS DEVICE AND METHOD

CROSS-REFERENCE TO RELATED APPLICATION(S)

This application is a divisional application of copending U.S. patent application Ser. No. 13/657,777, filed Oct. 22, 2012 which is incorporated herein by reference in its entirety.

FIELD OF THE INVENTION

This invention relates generally to spinal surgery, and more particularly to devices for stabilization of the spine in association with placement of an interbody construct for interbody fusion or the like.

BACKGROUND OF THE INVENTION

Varieties of interbody fusion devices are widely used following partial or total discectomies for stabilization of the spine at the site. Some stabilization devices are anchored to the pedicles. With several systems, the use of the pedicles requires screws or other anchoring devices that occupy significant space and involve muscle dissection and associated work-time for implantation. Nerve root injuries are a well-known potential complication of placement of screws in the pedicles.

The inter-spinous ("ISP") process devices are designed to increase the ISP height, thereby increasing the sagittal cross-sectional area of the foramen, where the nerve roots pass away out of the spine. It is thought that these devices may also unload the facet joints, and perhaps the intervertebral disc. They may limit spinal extension. This backward bending position may be painful for patients with spinal stenosis because it reduces the space available for the nerve roots in the exiting foraminal openings.

In addition to ISP implants, ISP fixation devices are also common to fix adjacent spinous processes to each other to stabilize the spinal motion-segment as an adjunct to spinal fusion. Current systems include spinous process plates that are fixed with adjacent spinous processes sandwiched therebetween.

SUMMARY

Presented herein is an implantable device for fixation of spinous processes. The device comprises first and second spaced plates, the first plate having a surface facing a surface of the second plate. The plates are configured for placement on either side of two adjacent spinous processes. In one aspect, the plates are held in place adjacent each side of the two spinous processes by a post connected to each of the plates and extending substantially therefrom the facing surface of the first plate to at least the facing surface of the second plate.

The device can also comprise a cage positionable between the first and second spaced plates, configured to maintain the spacing between the two adjacent spinous processes.

Related methods of operation are also provided. Other apparatuses, methods, systems, features, and advantages of the ISP device and the method of its use will be or become apparent to one with skill in the art upon examination of the following figures and detailed description. It is intended that all such additional apparatuses, methods, systems, features, and advantages be included within this description, be within the scope of the ISP device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 5 is a top plan view of the ISP fixation device of FIG. 3;

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Figure 26:
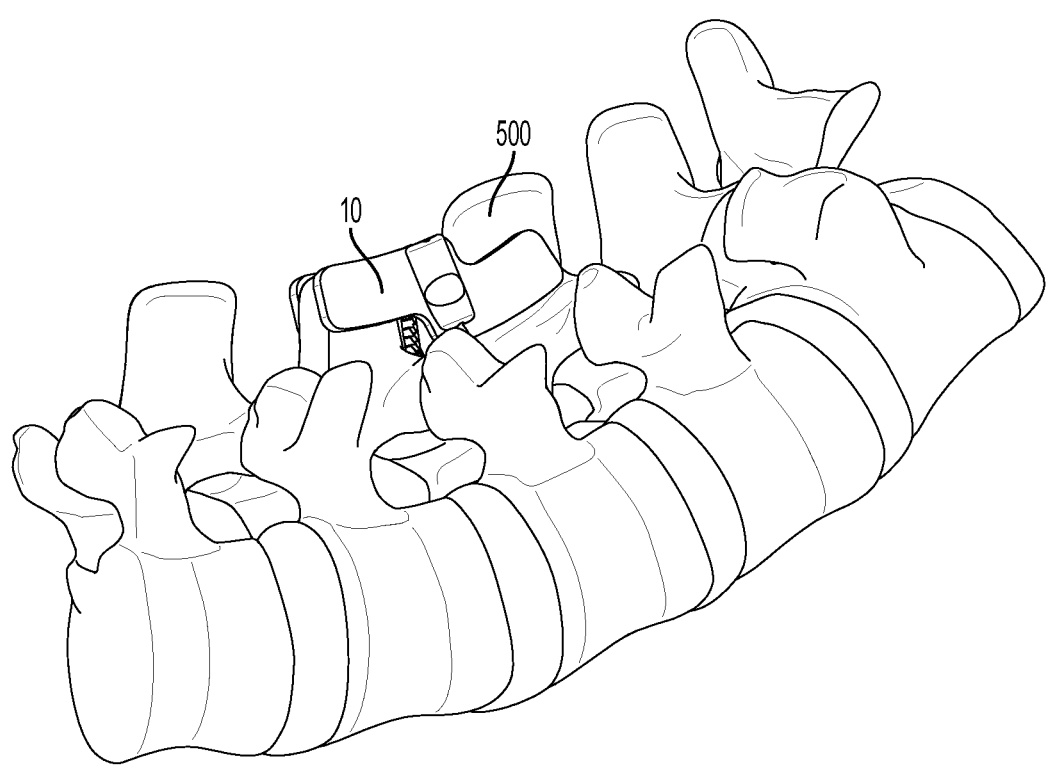
FIG. 26 is a perspective view of the final construct of an ISP fixation device in position using the method of FIGS. 24 and 25.
Figure 27:
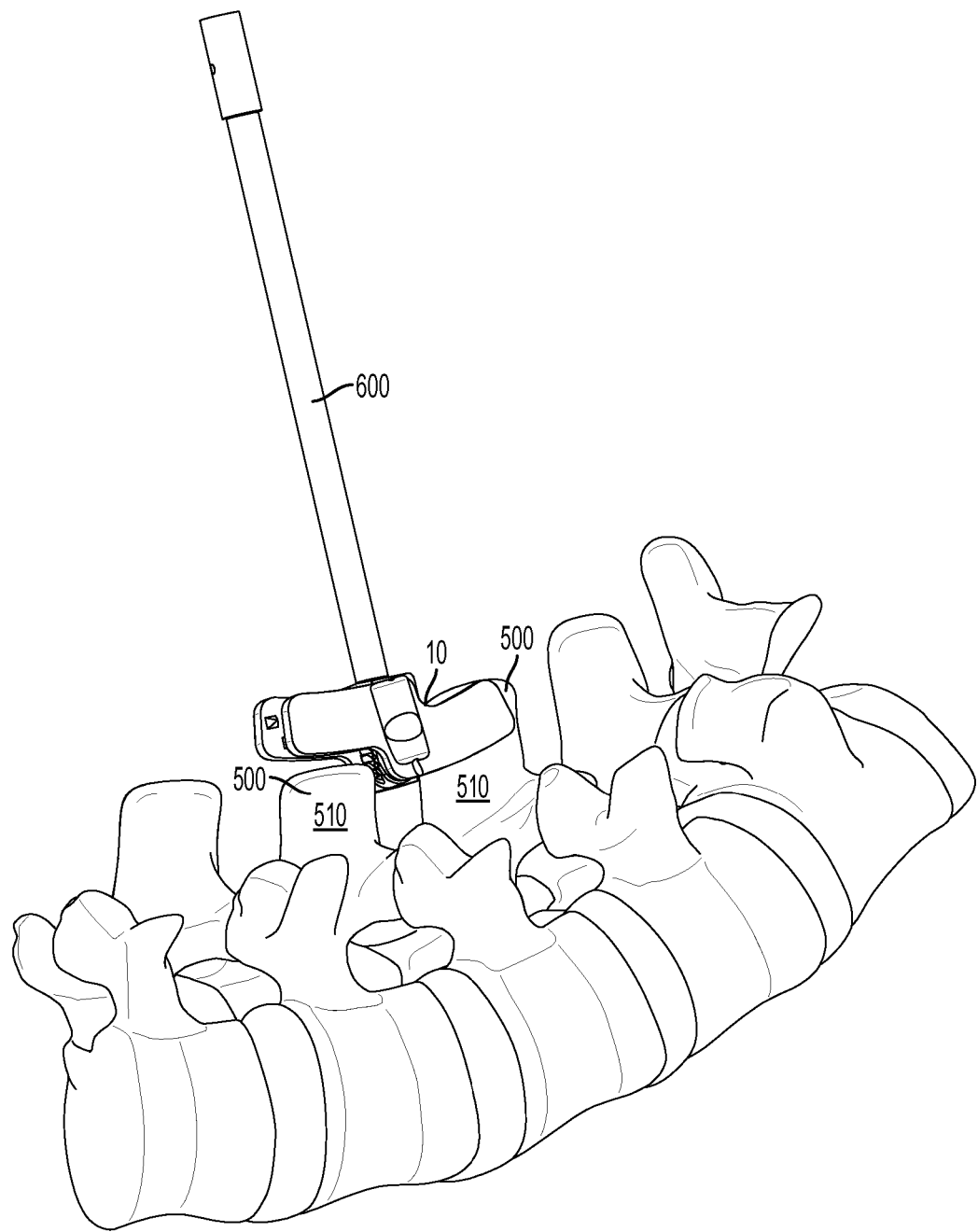
FIG. 27 is a perspective view of one aspect of a method of inserting an ISP fixation device where the ISP fixation device is placed between two adjacent spinous processes from a posterior-anterior direction.
Figure 28:
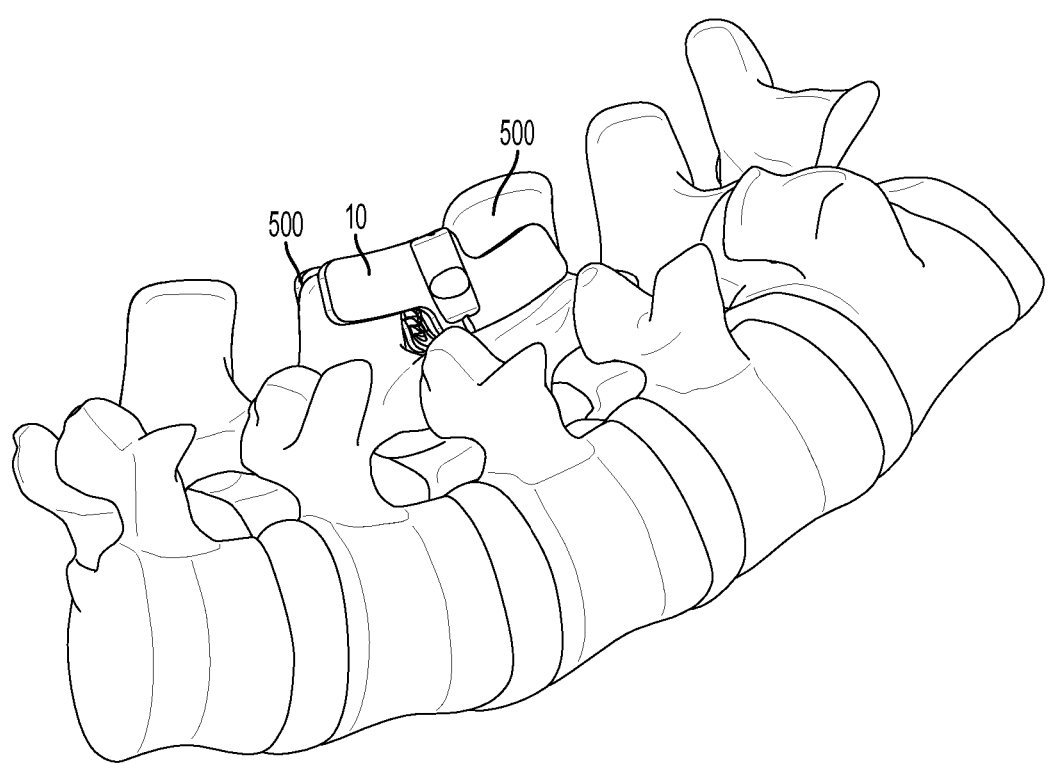
FIG. 28 is a perspective view of the final construct of an ISP fixation device in position using the method of FIGS. 24 and 27.

In one aspect, presented herein is an implantable device 10 for fixation of spinous processes. The device comprises first and second spaced plates 100, 200, the first plate 100 having a surface facing a surface of the second plate. The plates are configured for placement on either side of two adjacent spinous processes, as shown in FIG. 26. In one aspect, the plates are held in place adjacent each side 510 of the two spinous processes 500 by a post 300 connected to each of the plates and extending substantially therefrom the facing surface 110 of the first plate 100 to at least the facing surface 210 of the second plate 200. As can be appreciated, the post 300 may pass substantially through the facing surface 210 of the second plate, or completely through the second plate.

In one aspect, the connection of the post to the first plate 100 is pivotable to enable changing the attitude of the first plate relative to the second plate. As one in the art can appreciate, the sides of the spinous processes are not flat. As such, it may become necessary for the plates to be able to adjust the attitude of the first plate relative to the second plate. To accomplish this, in one aspect, the proximal end 310 of the post comprises a ball 315 and the first plate defines a socket 120 therein to retain the ball 315 and permit it to rotate.

In another aspect, the connection of the post to the second plate is adjustable to enable changing the spacing between the first plate 100 and the second plate. In this aspect, the second plate defines a bore 220 configured for receipt of the post. When positioned upon the post, the second plate can translate along its length in order to compress the device onto the spinous processes. Once in place, the use of a set screw or similar known fastener fixes the position of the second plate with respect to the first plate.

In an exemplified aspect, the device comprises a cage 400 positionable between the first and second spaced plates, configured to maintain the spacing between the two adjacent spinous processes. In one aspect, the cage 400 defines an interior cavity 409 and a graft window 413 on either the top portion 402 or the bottom portion 404, or both that is in communication with the interior cavity 409. As such, the interior cavity can be pre-packed with bone growth material that will assist in promoting bone growth from one of the spinous processes to the other via the cage 400.

Figure 12:
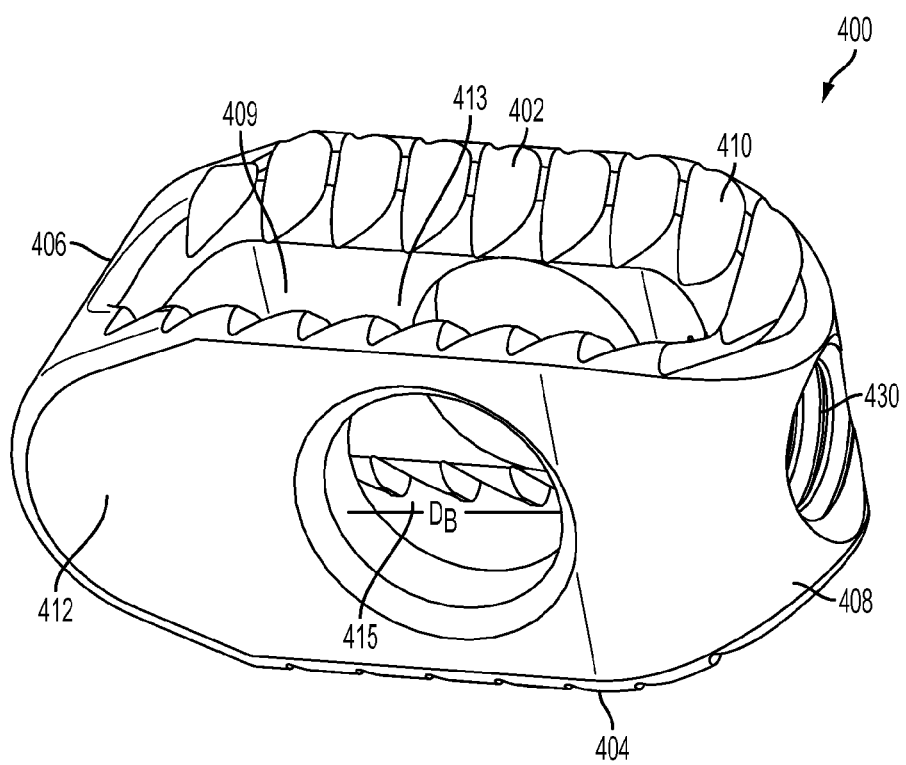
FIG. 12 is a perspective view of one aspect of a cage for use with an ISP fixation device, showing a post hole defined therein the side portion of the cage.
Figure 13:
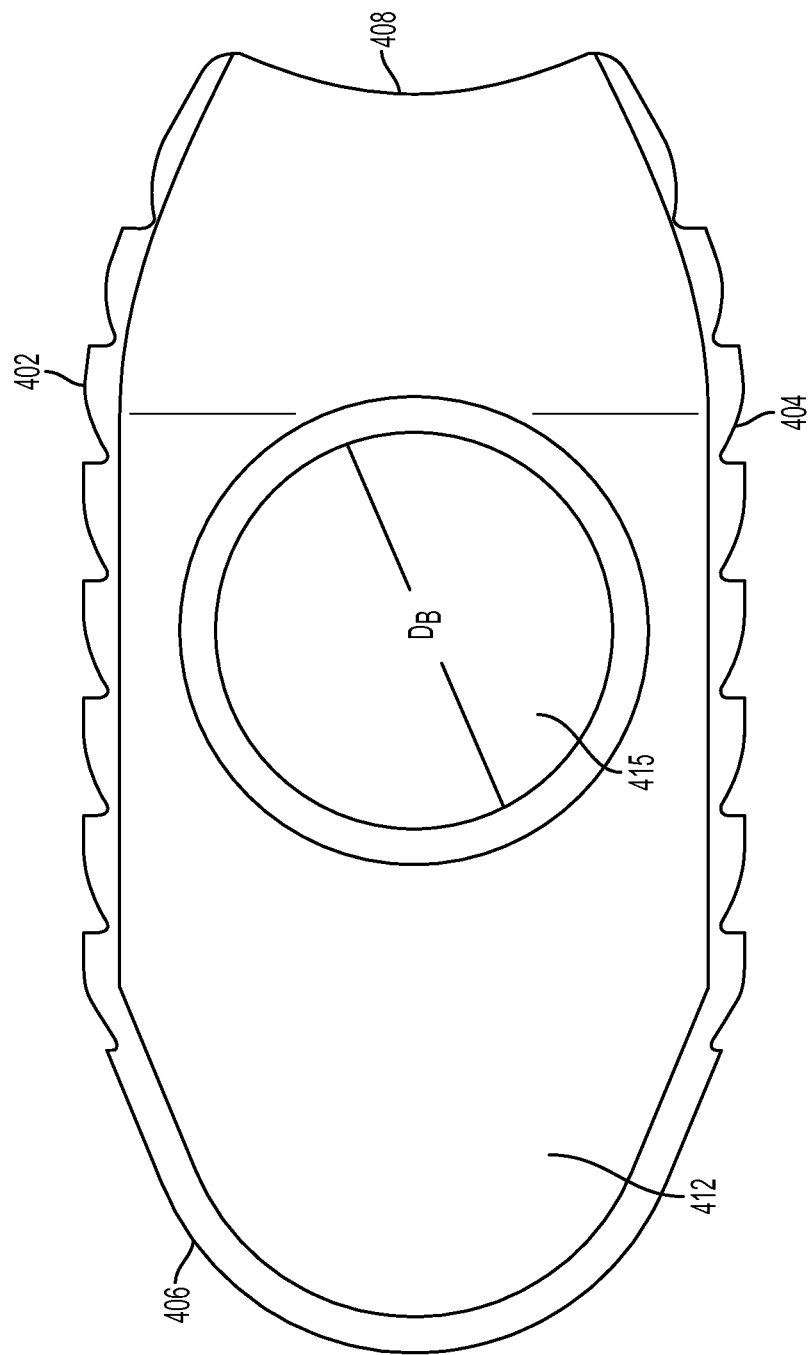
FIG. 13 is a side elevational view of the cage of FIG. 12.

As illustrated in FIG. 12, the top portion 402 and/or the bottom portion 404 of the cage can define ridges 410 that facilitate frictional engagement between the cage and the surrounding bony material. Additionally, at least portions of the top and/or bottom portion of the cage can be substantially concave when viewed from the leading or trailing end 408 to substantially conform to the shape of the adjacent spinous process(es).

In one exemplified aspect, as shown in FIG. 12, the two opposed side portions 412 of the cage 400 define a post bore 415 therethrough, where at least a portion of the post is configured to pass therethrough the post bore 415. In one aspect, the post has a snug fit with the post bore, but in another aspect, the post bore has a diameter $D_B$ larger than the diameter $D_P$ of the post such that the post is able to move within the post bore in a radial direction. In this aspect, if changing the spatial relationship of the plates has an impact on the attitude of the post and, as such, the post can somewhat move within the post bore 415 without affecting the placement of the cage. It is contemplated that the diameter of the post can be uniform or non-uniform.

Figure 14:
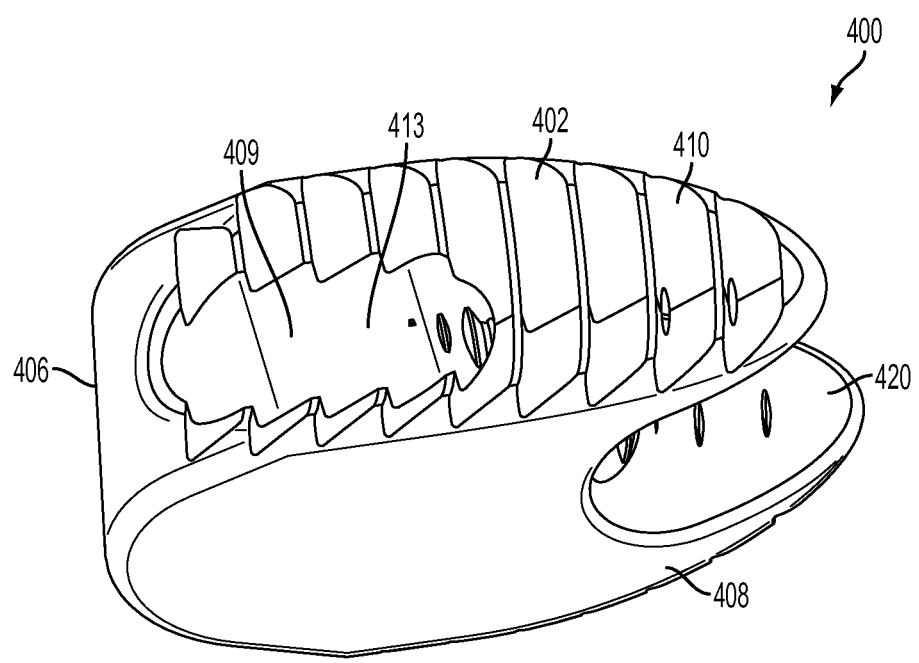
FIG. 14 is a perspective view of one aspect of a cage for use with an ISP fixation device, showing a post recess therein the trailing end of the cage.

FIG. 14 illustrates another aspect of the cage, where the trailing end 408 defines a post recess 420 configured to accept a portion of the post therein. In this aspect, the cage is positionable between the first and second spaced plates, whereby the portions of the cage 400 substantially adjacent the post recess 420 can, but don't necessarily, engage the post.

Figure 1:
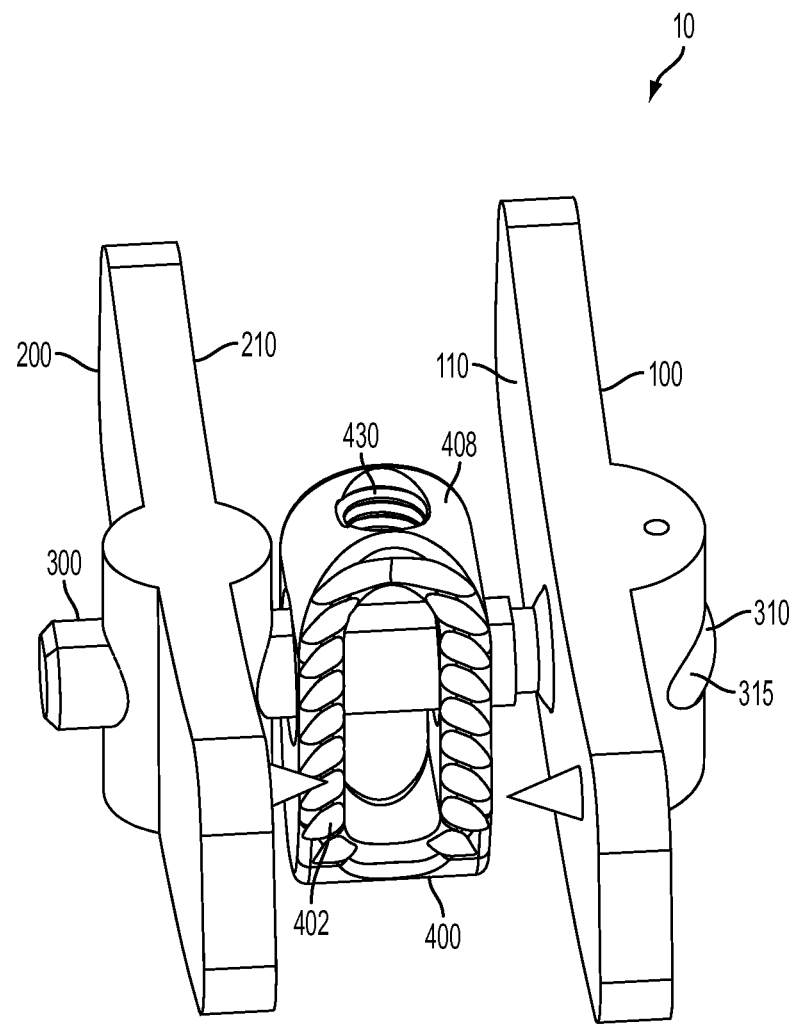
FIG. 1 is a perspective view of one aspect of an ISP fixation device.
Figure 2:
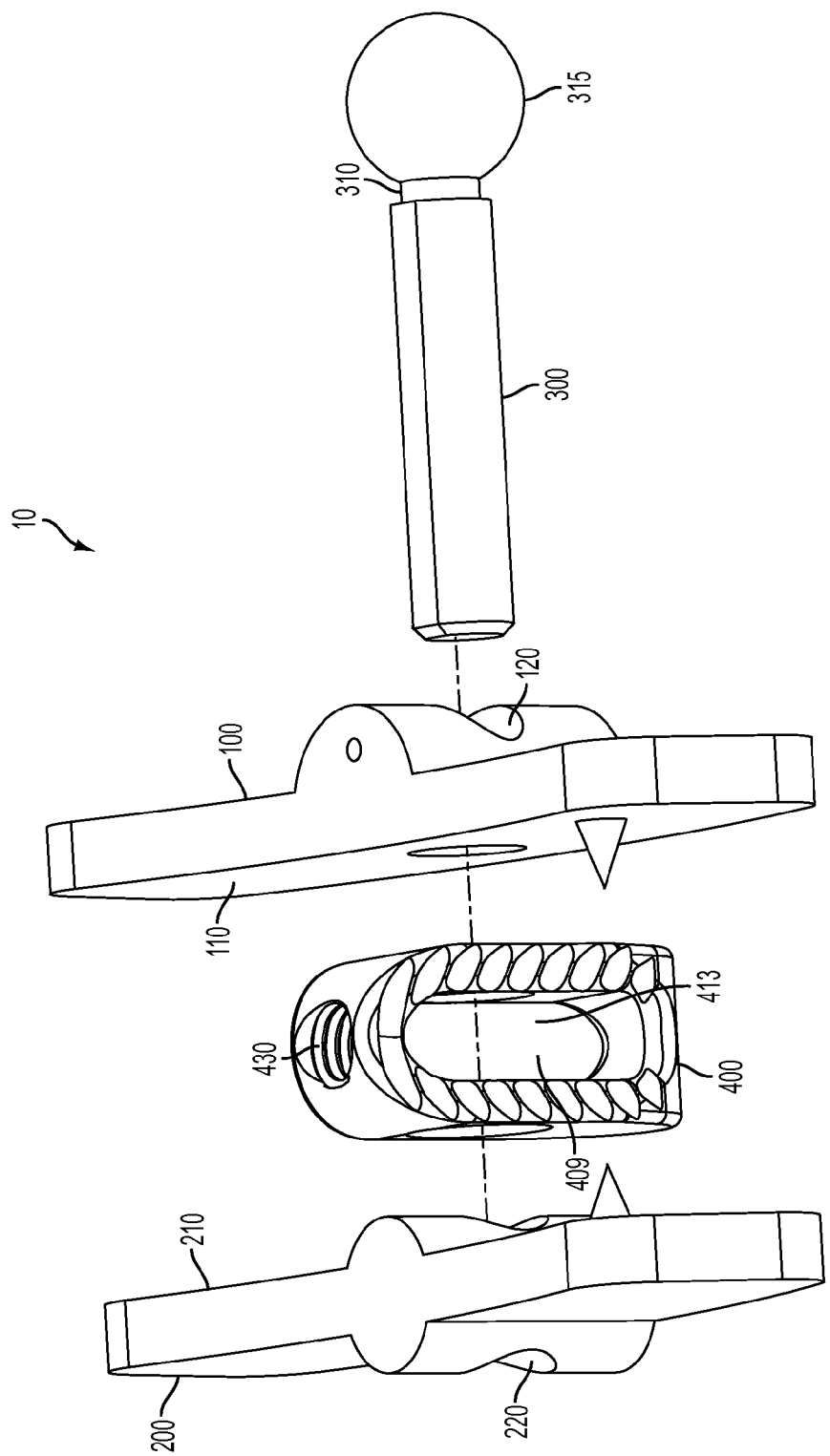
FIG. 2 is a partially exploded perspective view of the ISP fixation device of FIG. 1, showing two facing plates, a cage, and a rod to connect the first plate to the second plate.
Figure 3:
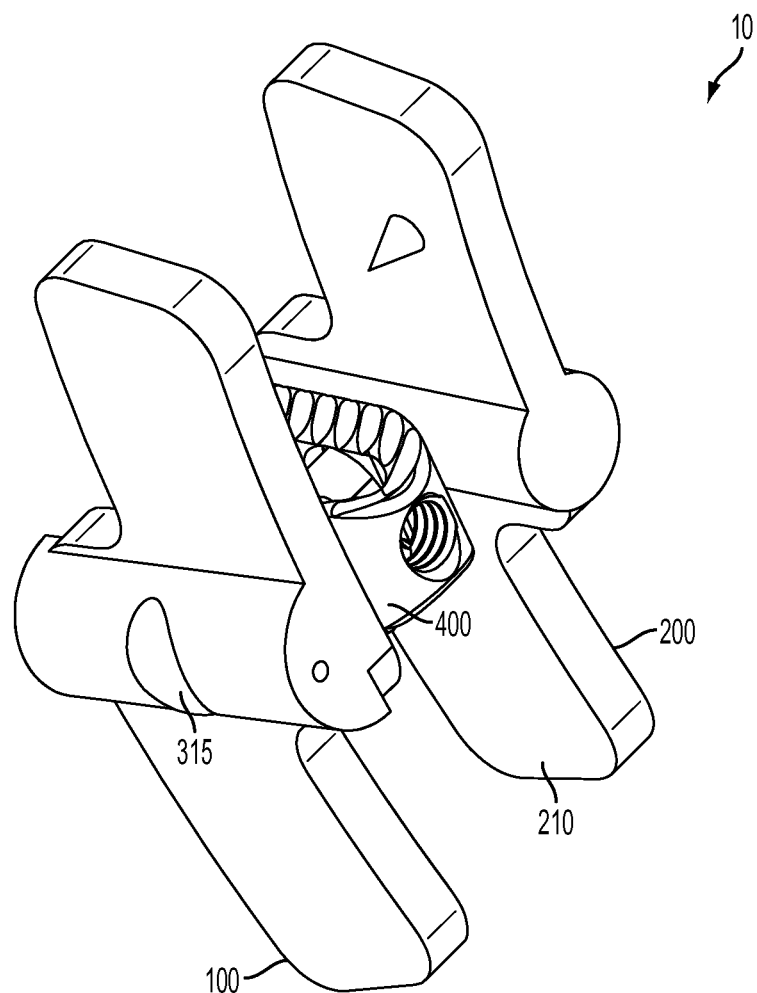
FIG. 3 is a perspective view of one aspect of an ISP fixation device having two plates that are substantially z-shaped.
Figure 4A:
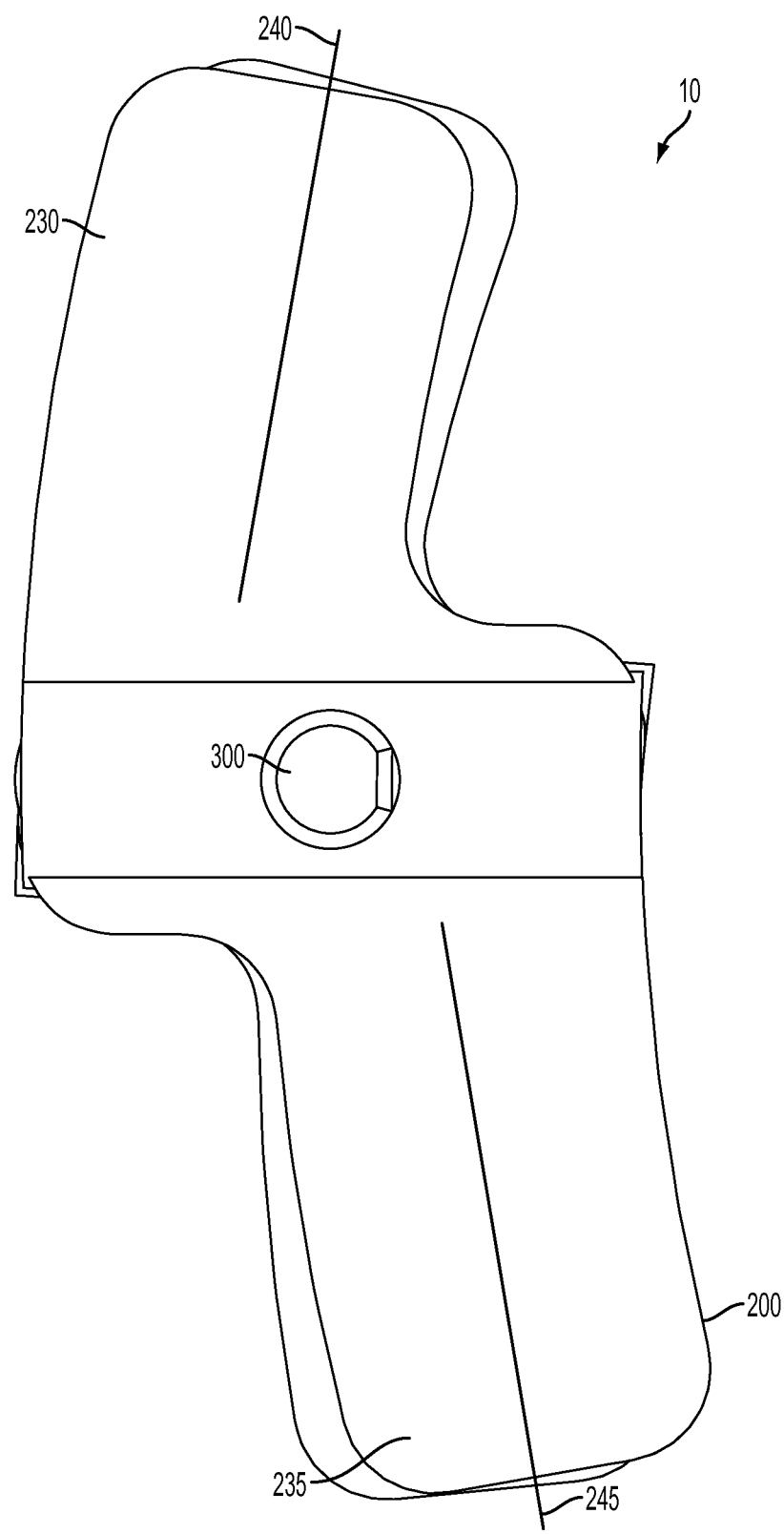
FIG. 4A is a side elevational view of the ISP fixation device of FIG. 3.
Figure 4B:
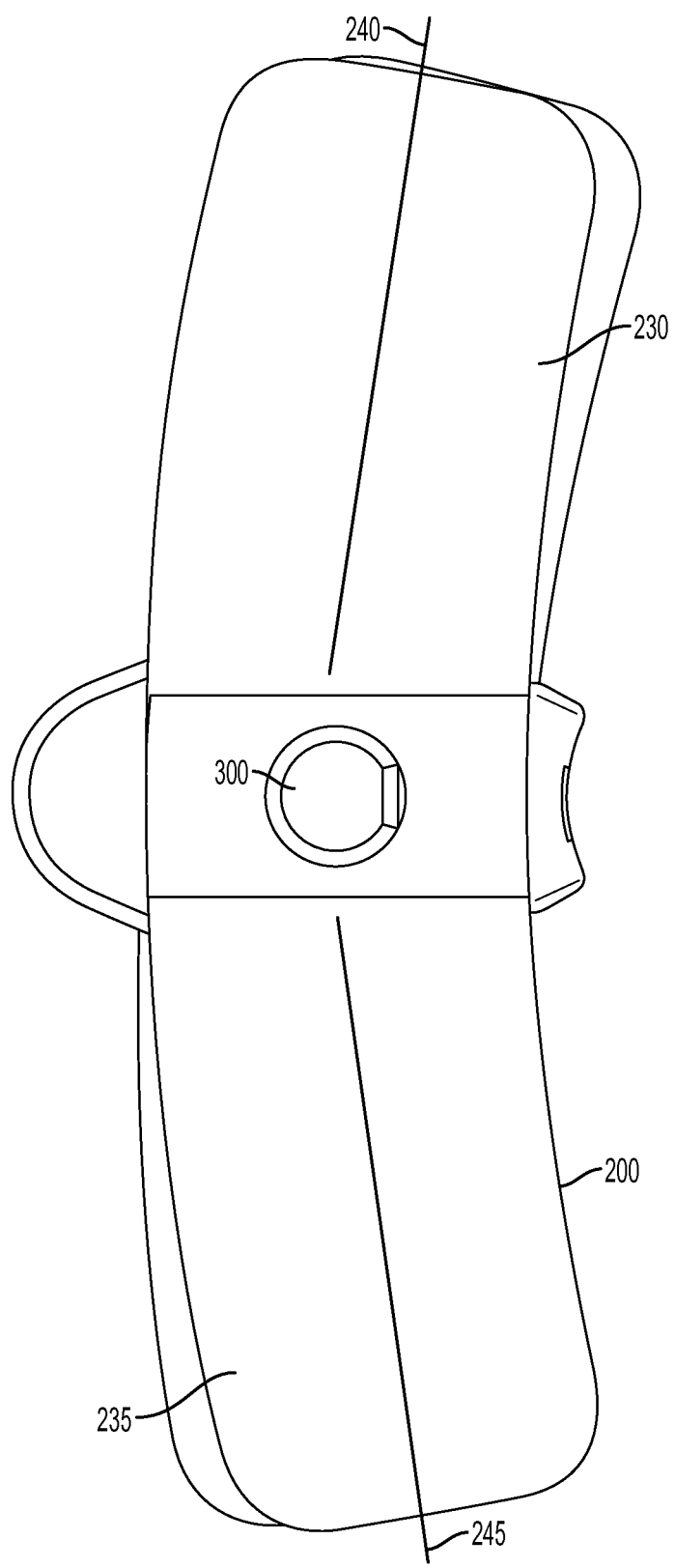
FIG. 4B is a side elevational view of an ISP fixation device where the two plates are substantially straight.
Figure 6:
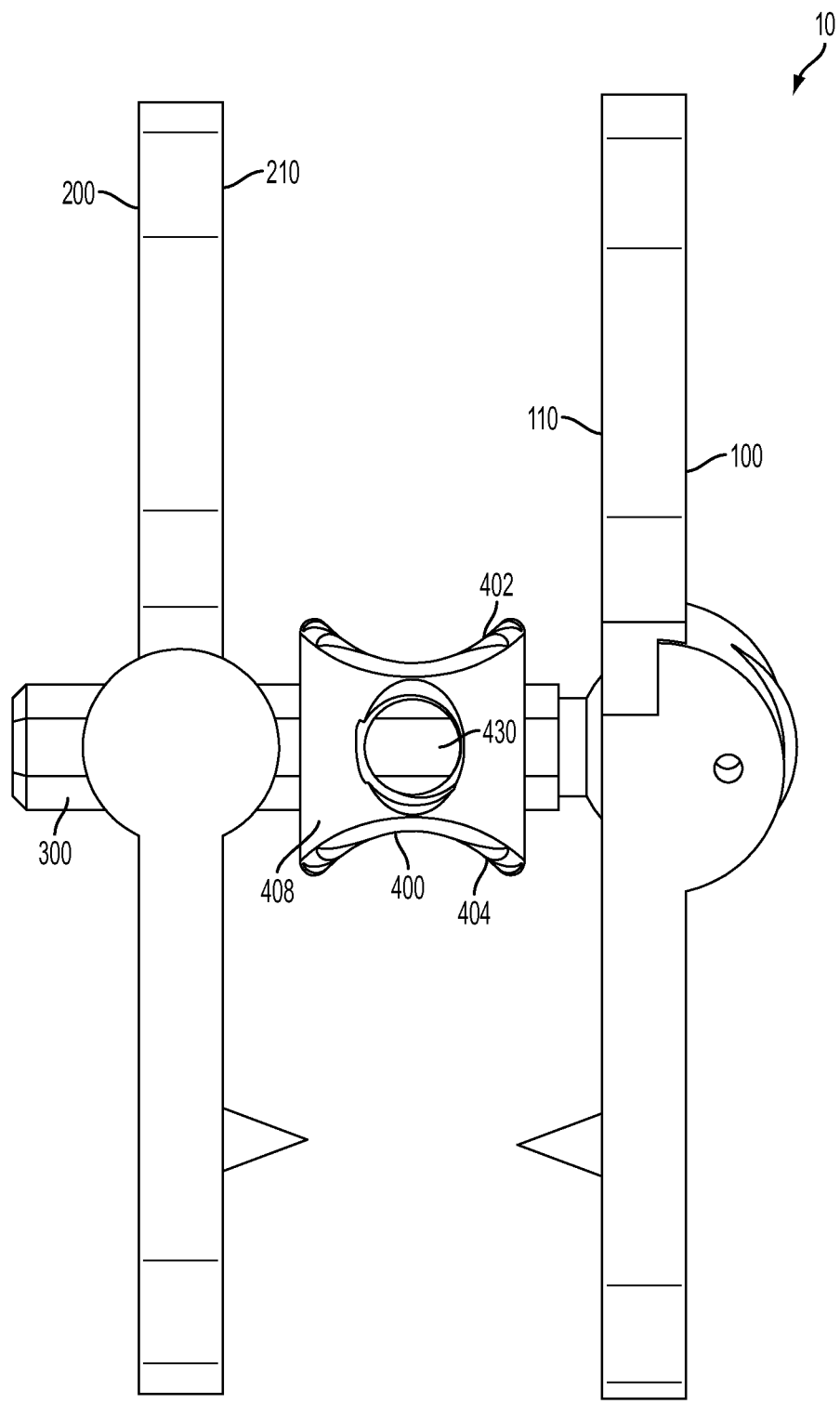
FIG. 6 is a rear elevation view of the ISP fixation device of FIG. 3.
Figure 7:
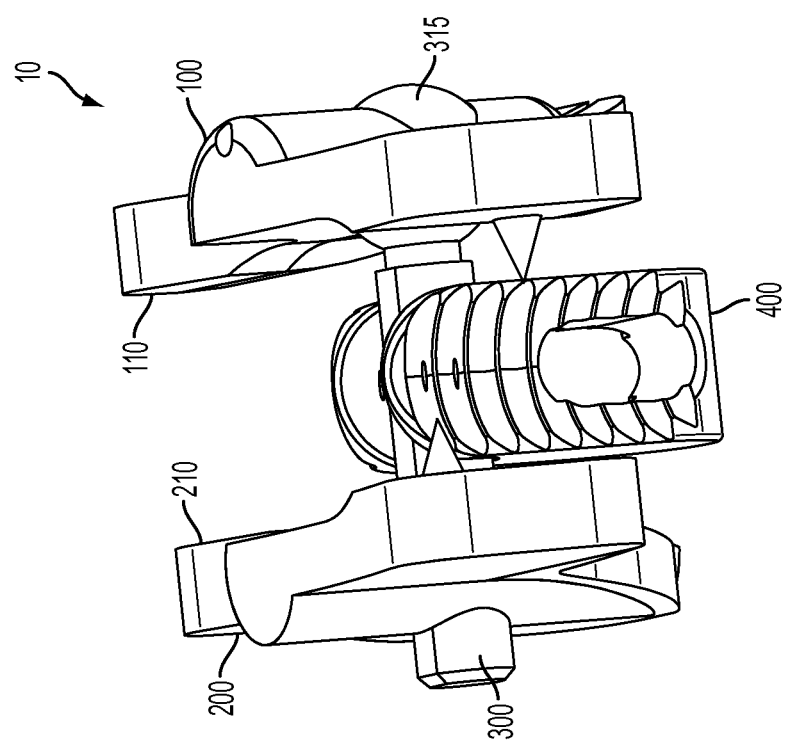
FIG. 7 is a perspective view of one aspect of an ISP fixation device showing a cage having a post recess in its trailing end.

In still another aspect, the first and second spaced plates each have an upper portion 130, 230 and a lower portion 135, 235, where each upper portion has an upper portion longitudinal axis 140, 240 and each lower portion has a lower portion longitudinal axis 145, 245. In this particular aspect, as shown in FIG. 4A, at least one of the upper portion longitudinal axes is substantially collinear with the respective lower portion longitudinal axis. By substantially collinear, it is meant that the upper portion and lower portion are substantially one over another. It is understood that each portion of the plate may have a curvature. As such, the longitudinal axes may not be exactly collinear. In yet another aspect, as illustrated in FIG. 4B, at least one of the upper portion longitudinal axes is substantially parallel to, but not collinear with, the respective lower portion longitudinal axis. Again, by substantially parallel, it is meant that upper portion and lower portion are not substantially directly over one another.

Figure 8:
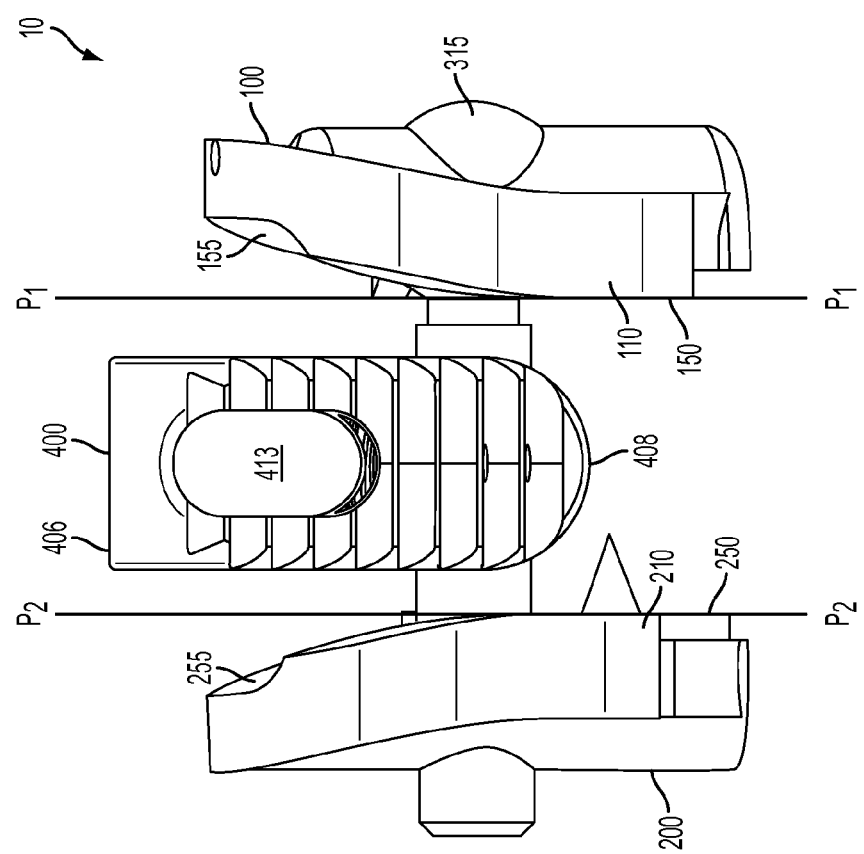
FIG. 8 is a top plan view of the ISP fixation device of FIG. 7, showing second portions of each of the spaced plates being flared from the first and second planes, respectively.

In one aspect, the first and second spaced plates are substantially planar. By substantially planar, it is meant that a substantial portion of the respective facing surface of the respective plate lies in the same plane. In another aspect, first portions 150 of the facing surface 110 of the first plate are in a first plane $P_1$ and first portions 250 of the facing surface 210 of the second plate are in a second plane $P_2$. In this aspect, as shown in FIG. 8, second portions 155, 255 of the facing surface of at least one of the first or second plates are flared away and lie in a plane that is angled with respect to the respective first or second plane such that, when the device is implanted, the plates substantially conform to the shape of the spinous processes.

Figure 9:
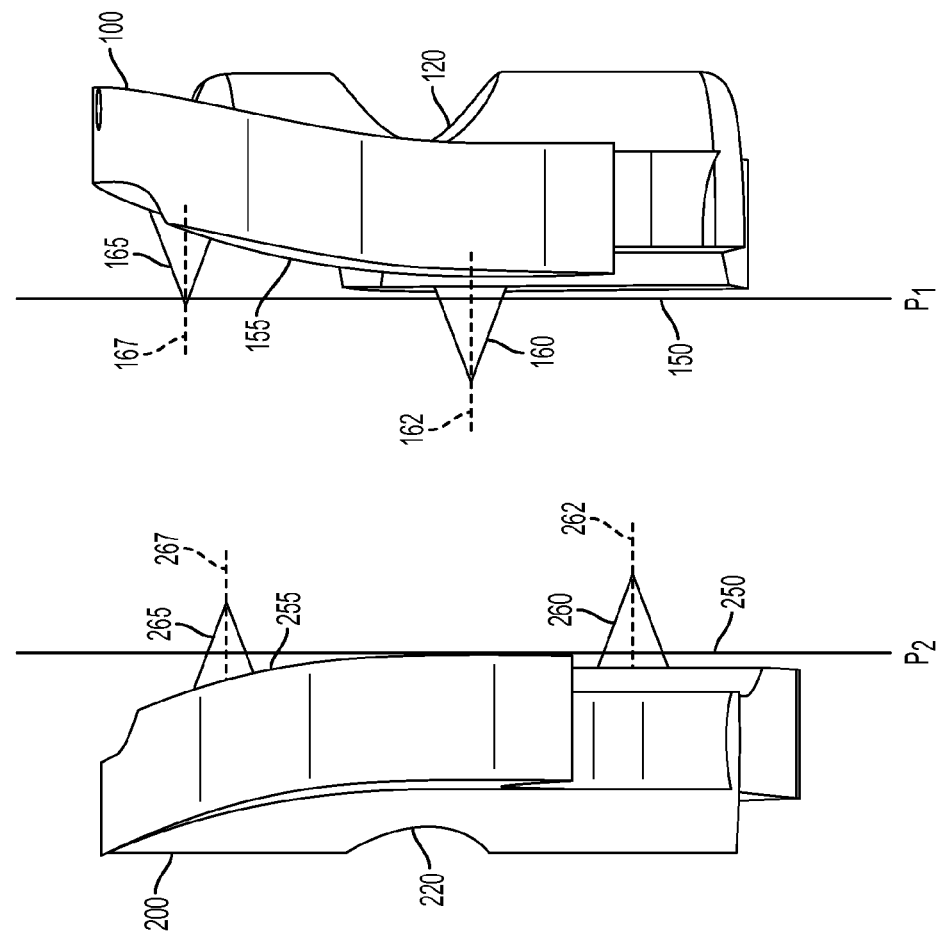
FIG. 9 is a top plan view of the two opposing plates of the ISP fixation device of FIG. 8.
Figure 10:
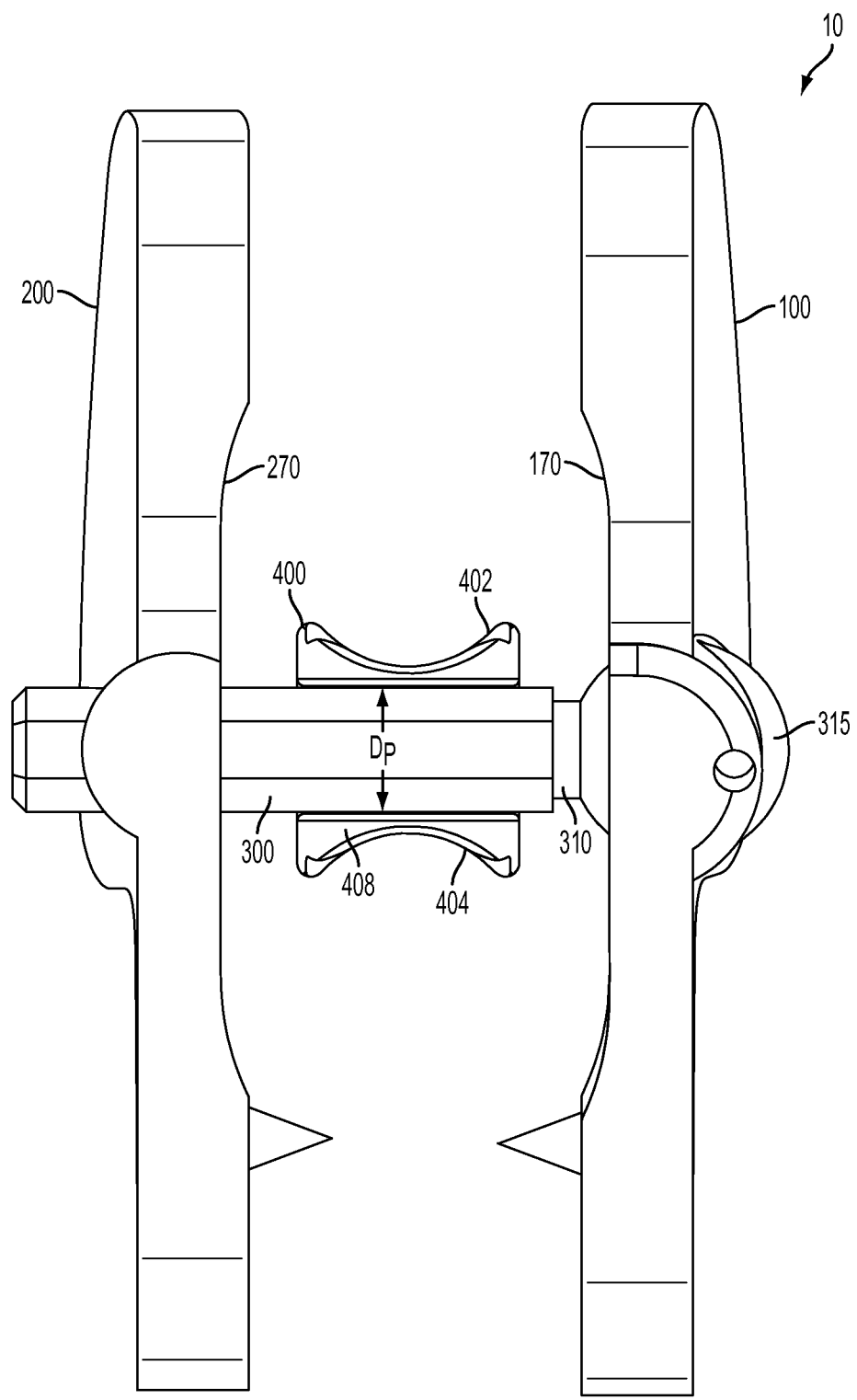
FIG. 10 is a rear elevational view of the ISP fixation device of FIG. 8.
Figure 11:
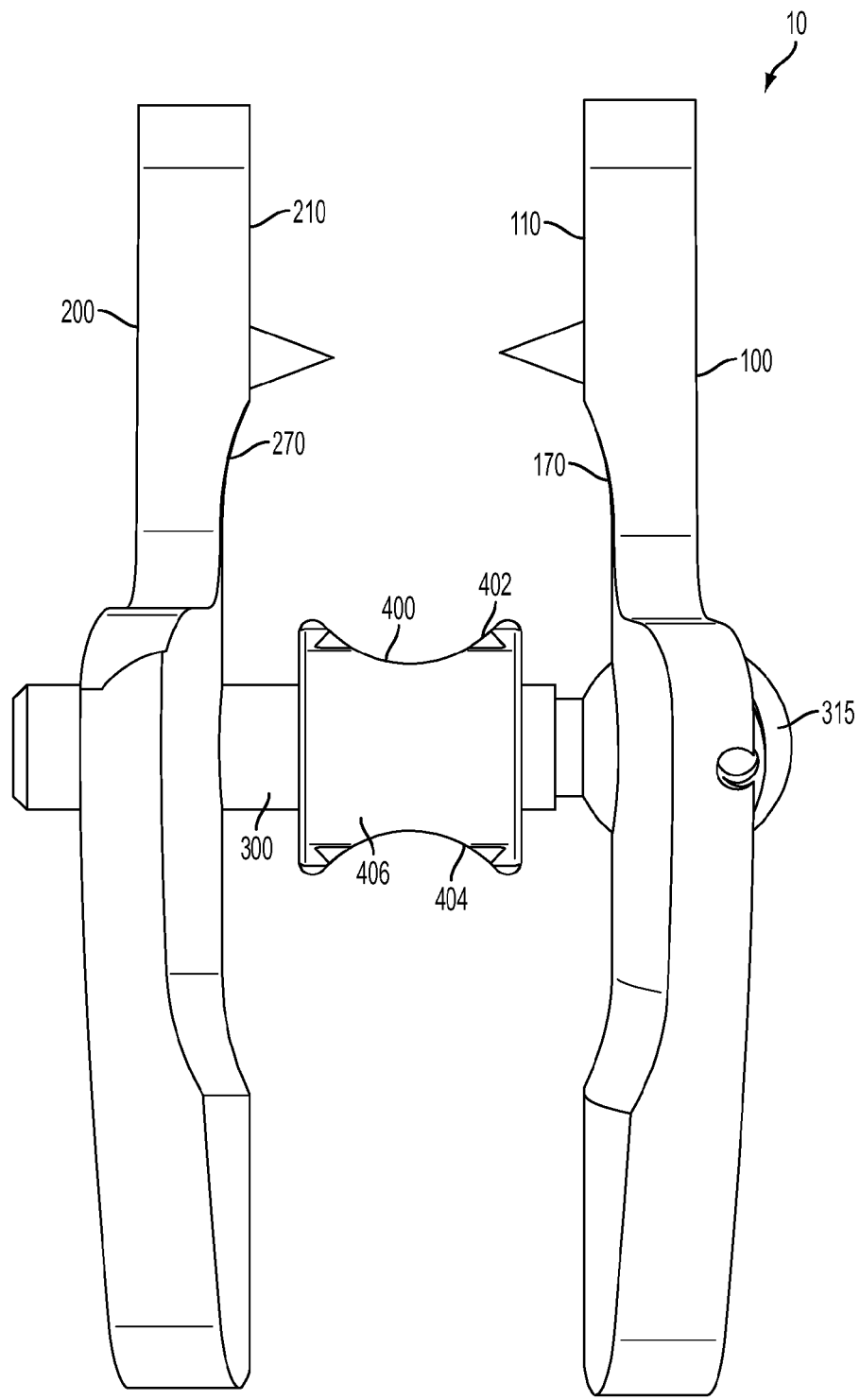
FIG. 11 is a front elevational view of the ISP fixation device of FIG. 8.

As can be seen in FIG. 9, the first or second plate can also have at least one first bone engaging spike 160, 260 protruding from and substantially transverse to at least one of the first portions of the facing surfaces. In one aspect, there can also be at least one second bone engaging spike 165, 265 protruding from at least one second portion of at least one facing surfaces. In yet another aspect, the at least one second bone engaging spike has a longitudinal axis 167, 267 that is substantially parallel to the longitudinal axis 162, 262 of the at least one first bone engaging spike. This arrangement, while not required, assists the device in engaging the spinous process. As one skilled in the art can appreciate, there may be a plurality of spikes protruding from any of the aforementioned portions of the facing surfaces.

It is also contemplated that the portions 170, 270 of the facing surface substantially near the implant, when assembled, can be recessed to accommodate the positioning of the cage.

The devices described above can make up portions of a system for fixation of spinous processes. The system, in one aspect, comprises an elongate insertion tool 600, first and second plates, a post, and a cage as described above, where the cage defines a post bore therethrough. In this aspect, the trailing end 408 of the cage 400 can define a tool bore 430 configured to engage the distal end 610 of the elongate insertion tool 600.

In one aspect of this system, when the distal end 610 of the elongate insertion tool is engaged with the cage and the cage is positioned on a portion of the post, portions of the distal end of the elongate insertion tool maintain a spatial relationship between the cage and the first and second spaced plates. In this aspect, the insertion tool 600 prevents the cage from migrating along the post to be substantially closer to one of the plates.

Figure 18:
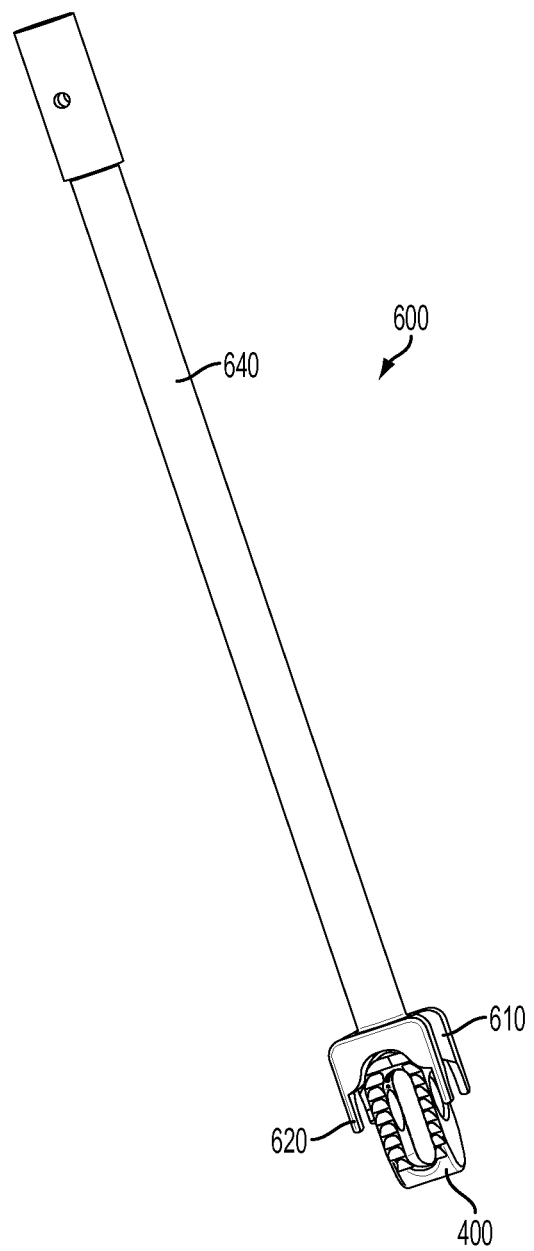
FIG. 18 is a perspective view of one aspect of an insertion tool for use with an ISP fixation device, shown in engagement with a cage.
Figure 19:
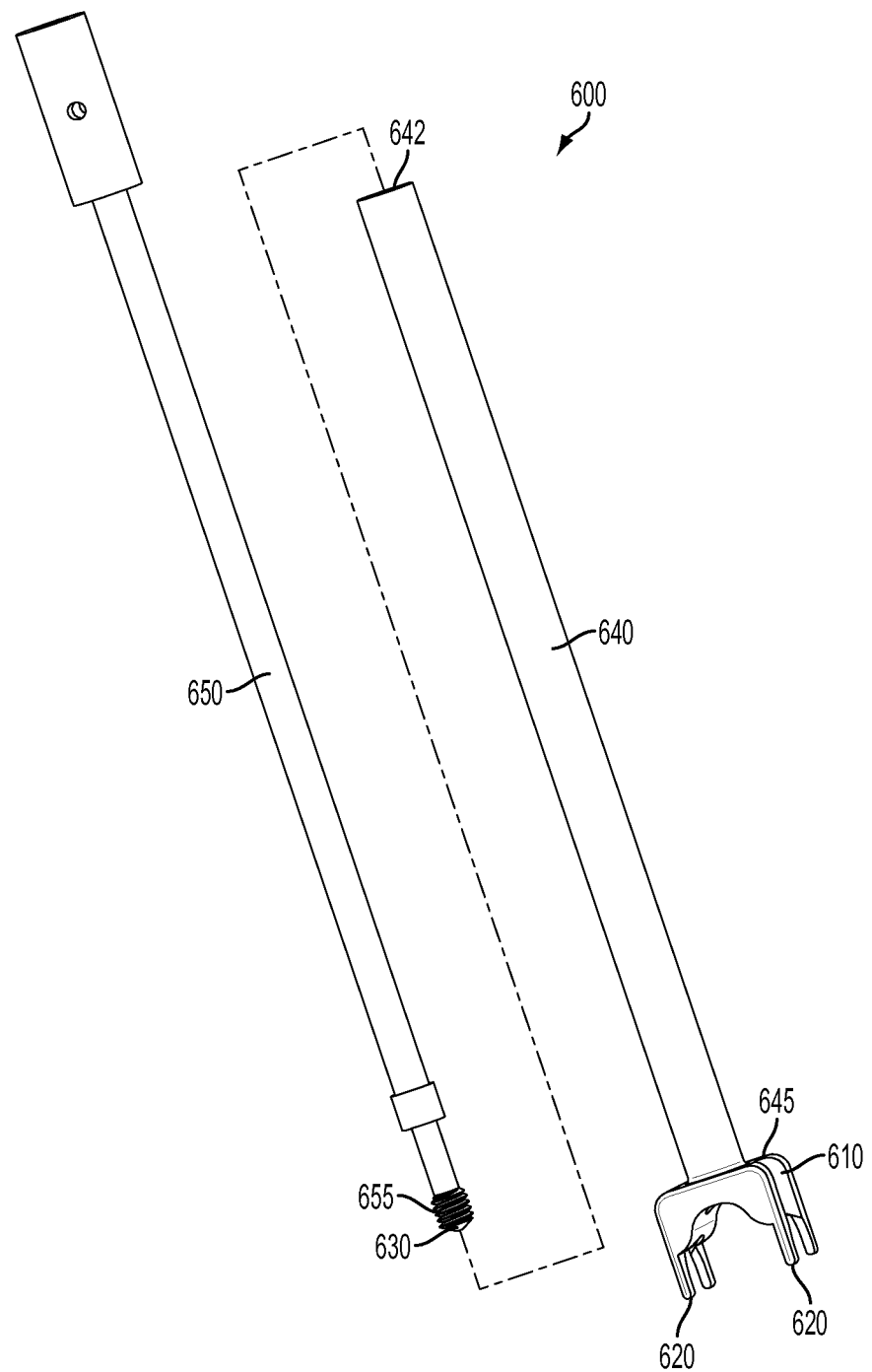
FIG. 19 is a partially exploded perspective view of the insertion tool of FIG. 18.
Figure 20:
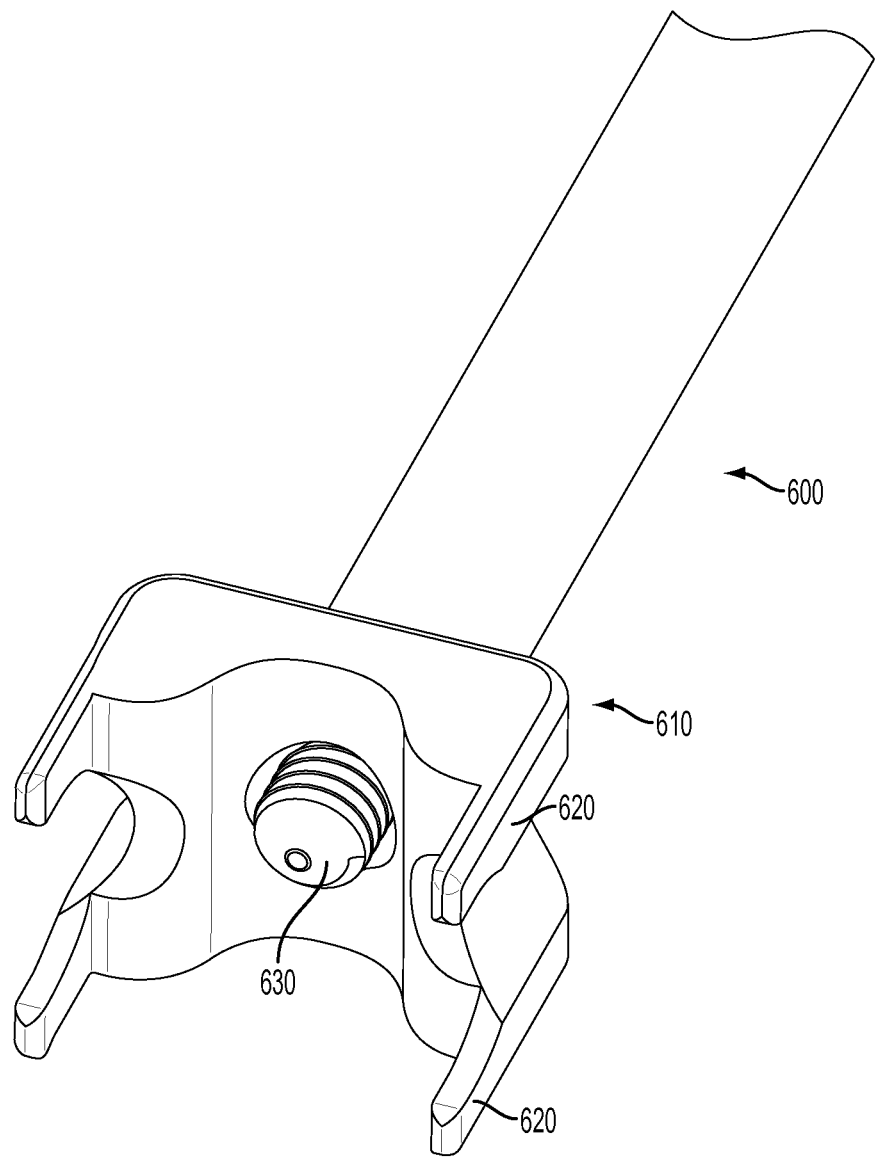
FIG. 20 is a perspective view of the distal end of the insertion tool of FIG. 18, showing two pairs of spaced legs and a male protrusion.
Figure 21:
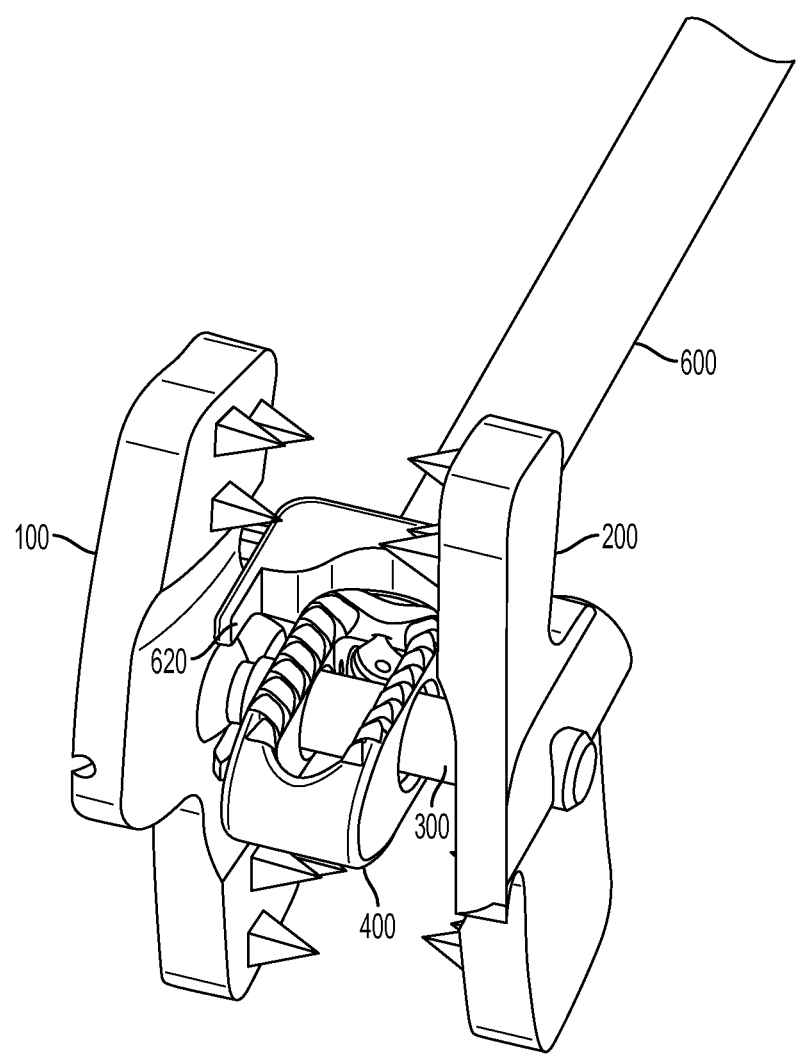
FIG. 21 is a perspective view of the distal end of the insertion tool of FIG. 18 in engagement with an ISP fixation device, showing the legs of distal end of the insertion tool keeping the two spaced plates in a spatial relationship with the cage.
Figure 22:
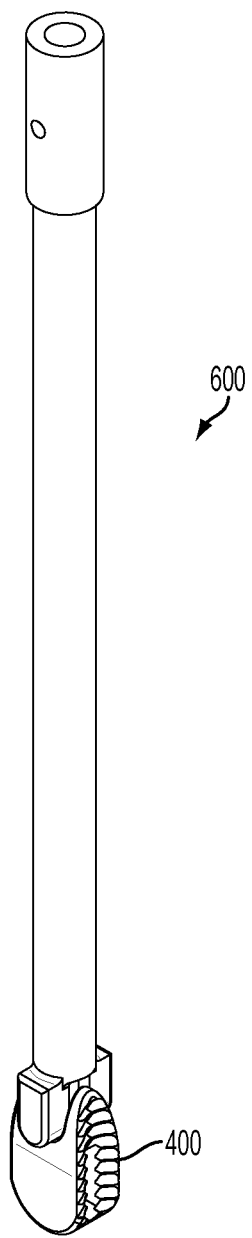
FIG. 22 is a perspective view of one aspect of an insertion tool in engagement with a cage having a post recess in its trailing end.
Figure 23:
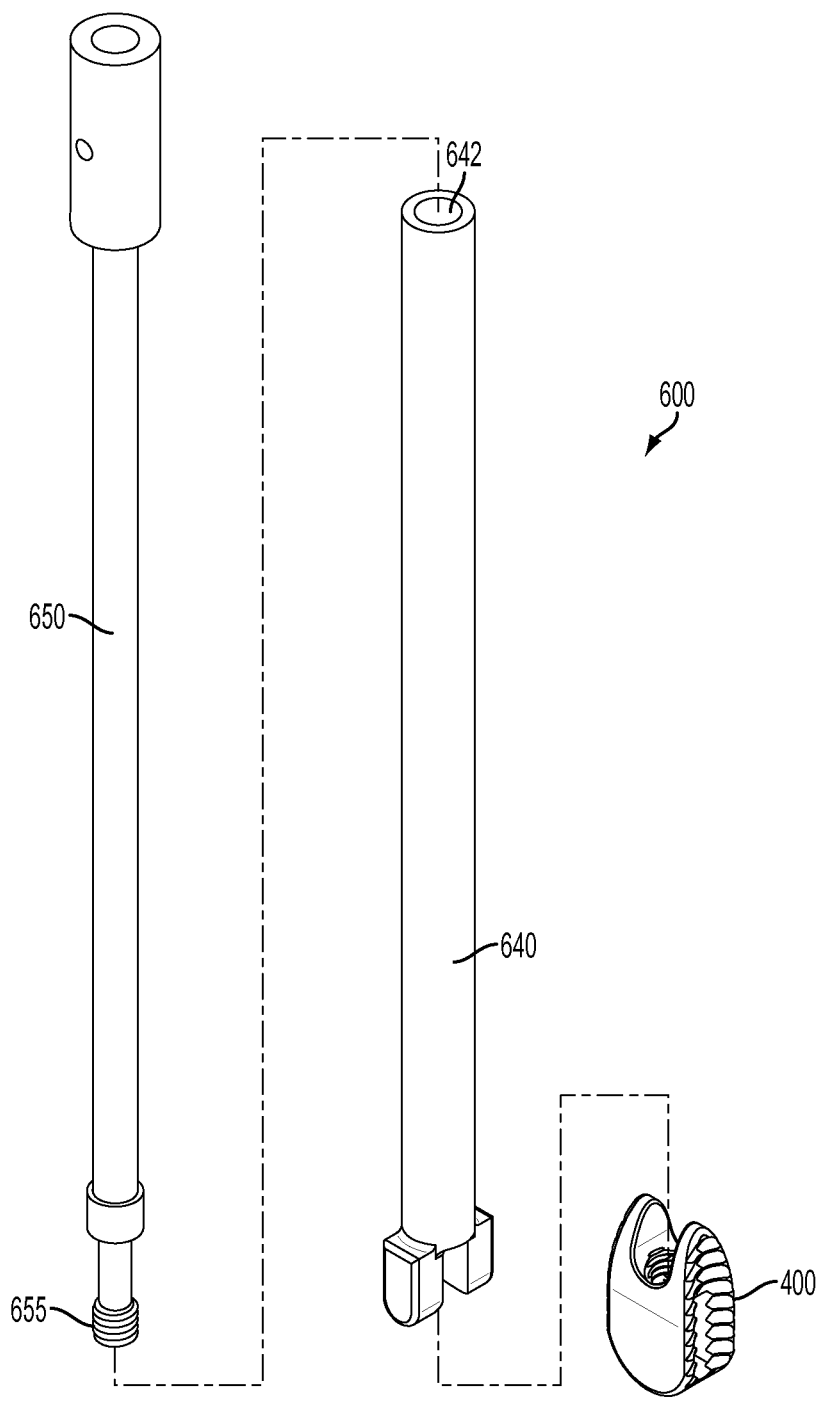
FIG. 23 is a partially exploded perspective view of the insertion tool and cage of FIG. 22.

In an exemplified aspect, the elongate insertion tool comprises at least two pairs of legs 620 extending therefrom the distal end 610 and a male protrusion 630 extending along a longitudinal axis of the elongate insertion tool. The male protrusion 630 is configured to engage the tool bore 430 of the cage 400 and, when engaged with the cage, one of the at least two pairs of legs 620 is spaced from the cage in a direction transverse to the longitudinal axis of the elongate insertion tool 600, and another of the at least two pairs of legs 620 is oppositely spaced from the cage. This relationship is illustrated in FIG. 18.

As one in the art can appreciate, the male protrusion of the insertion tool can be threaded to engage threaded portions of the tool bore 430 of the cage. In another aspect, the insertion tool can comprise an insertion sleeve 640 defining an interior longitudinal cavity 642 and an insertion rod 650 configured to be positioned within the interior longitudinal cavity. In one aspect, the male protrusion 630 comprises the distal end 655 of the insertion rod 650, which can be rotated with respect to the insertion sleeve 640. In this aspect, the pairs of legs described above can be integral with or merely connected to the distal end 645 of the insertion sleeve.

Also presented herein is a posterior-anterior method of using the system above to fixate two adjacent spinous processes. In one aspect, the method comprises accessing an area substantially near the first and second spaced spinous processes. The surfaces of the adjacent spinous process can then be prepared. In one aspect, a rasp 700 is used to remove portions of bone on one or both spinous process. Once the space is prepared, the insertion tool 600 is engaged with the trailing end of the cage 400 by screwing the distal end 655 of the insertion rod into the tool bore. The post is then inserted into the post bore, positioning the first plate 100 adjacent the cage, but spaced therefrom by the legs 620 of the distal end 610 of the insertion tool. At this point, the second plate is positioned thereon the post adjacent the opposite side of the cage, also spaced therefrom by the legs of the distal end 610 of the insertion tool. At this point, the entire construct is then positioned in the desired position where the cage is inserted between the two spinous processes (leading end 406 first) and the plates are positioned on opposing sides of the two spinous processes. Once positioned, the insertion tool 600 can be removed and the first and second plates can be compressed to exert the desired force on the spinous processes. At this point, the second plate is fixated onto the post.

In another aspect, a system for fixation of spinous processes can comprise an elongate insertion tool, first and second plates, a post, and a cage 400 as described above, where the trailing end of the cage defines a post recess. In this aspect, the trailing end 408 of the cage can also define a tool bore 430 configured to engage the distal end 610 of the elongate insertion tool. As one in the art can appreciate, the distal end 610 of the insertion tool 600 can be threaded to engage threaded portions of the tool bore of the cage 400.

Also presented herein is a posterior-anterior method of using the system above to fixate two adjacent spinous processes. In one aspect, the method comprises accessing an area substantially near the first and second spaced spinous processes. The surfaces of the adjacent spinous process can then be prepared. In one aspect, a rasp 700 is used to remove portions of bone on one or both spinous process. Once the space is prepared, the insertion tool is engaged with the trailing end of the cage by screwing the distal end of the insertion tool into the tool bore. The cage is then positioned in the desired position where the cage is inserted between the two spinous processes. The first and second plates can be assembled together before insertion and positioned where the post is engaged with the post recess 420 and the plates are positioned on opposing sides of the two spinous processes. Once positioned, the insertion tool 600 can be removed and the first and second plates can be compressed to exert the desired force on the spinous processes. At this point, the second plate is fixated onto the post.

Figure 15:
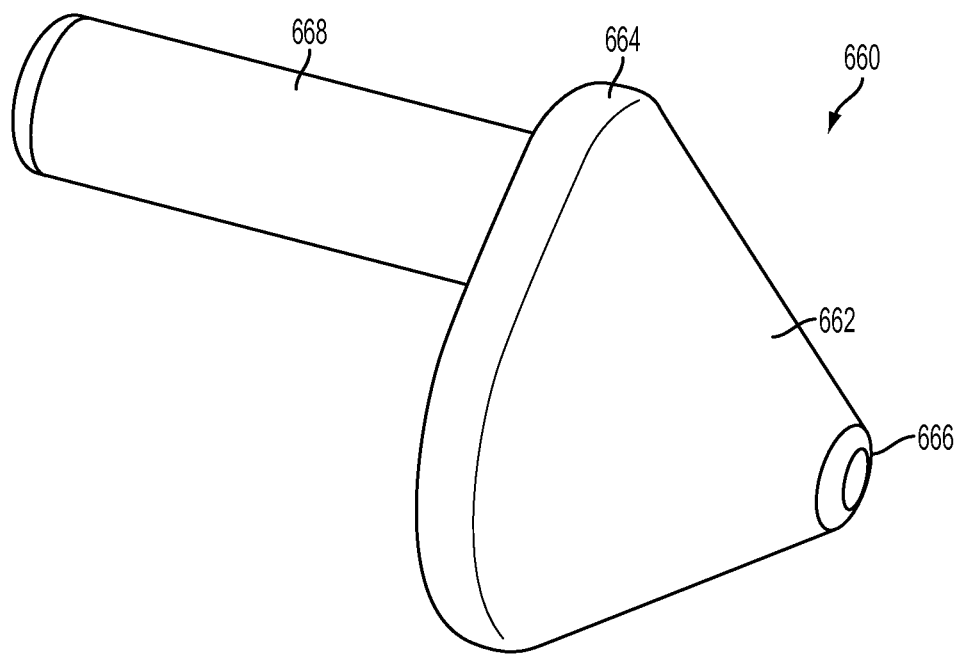
FIG. 15 is a perspective view of one aspect of an inserter for inserting a cage between two adjacent spinous processes using a lateral approach.
Figure 16:
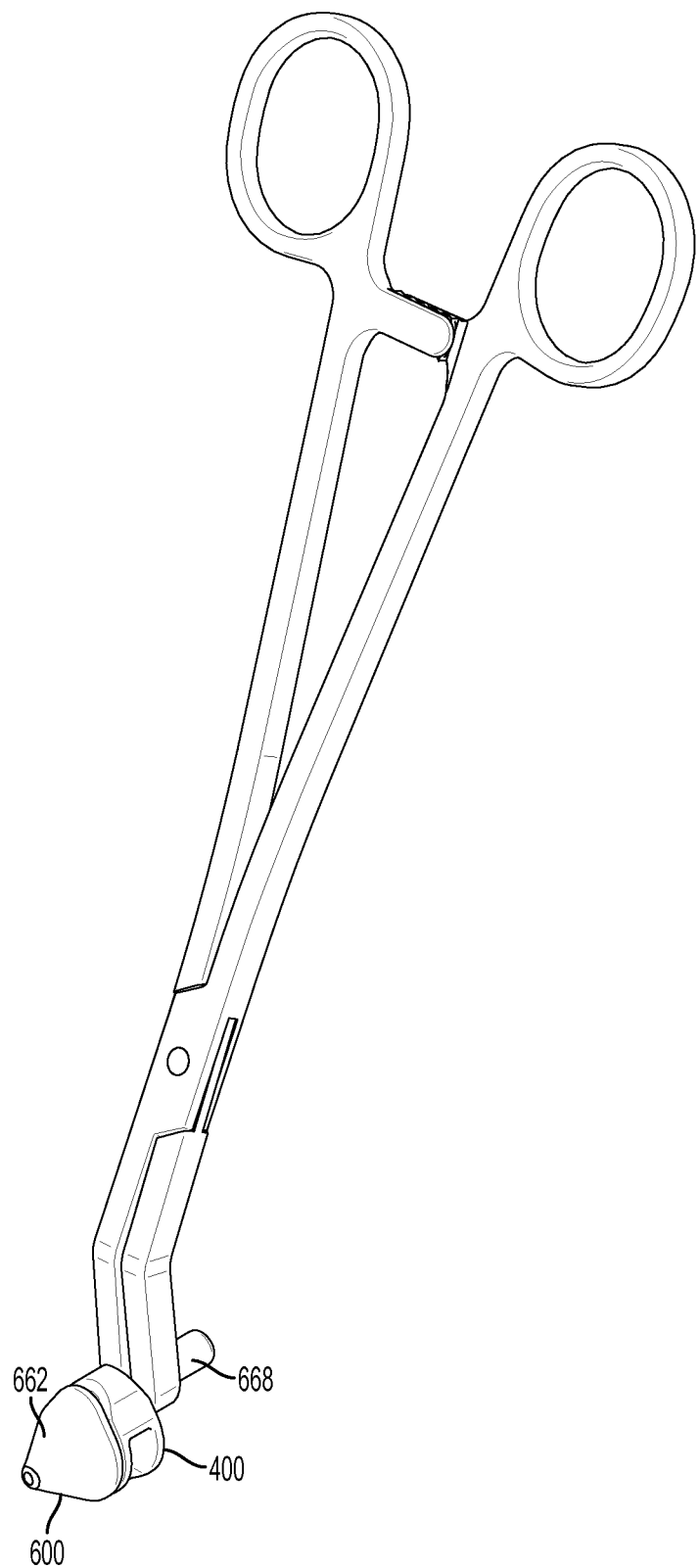
FIG. 16 is a perspective view of one aspect of an inserter in engagement with a cage, being held by surgical forceps.
Figure 17:
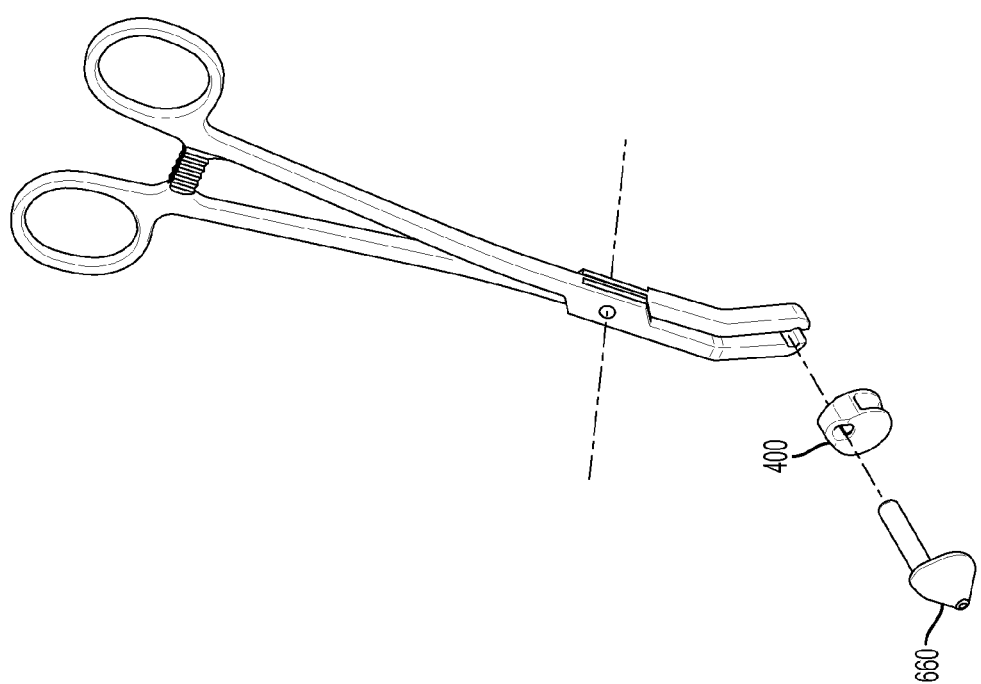
FIG. 17 is a partially exploded perspective view of the inserter, cage, and forceps of FIG. 16.
Figure 29:
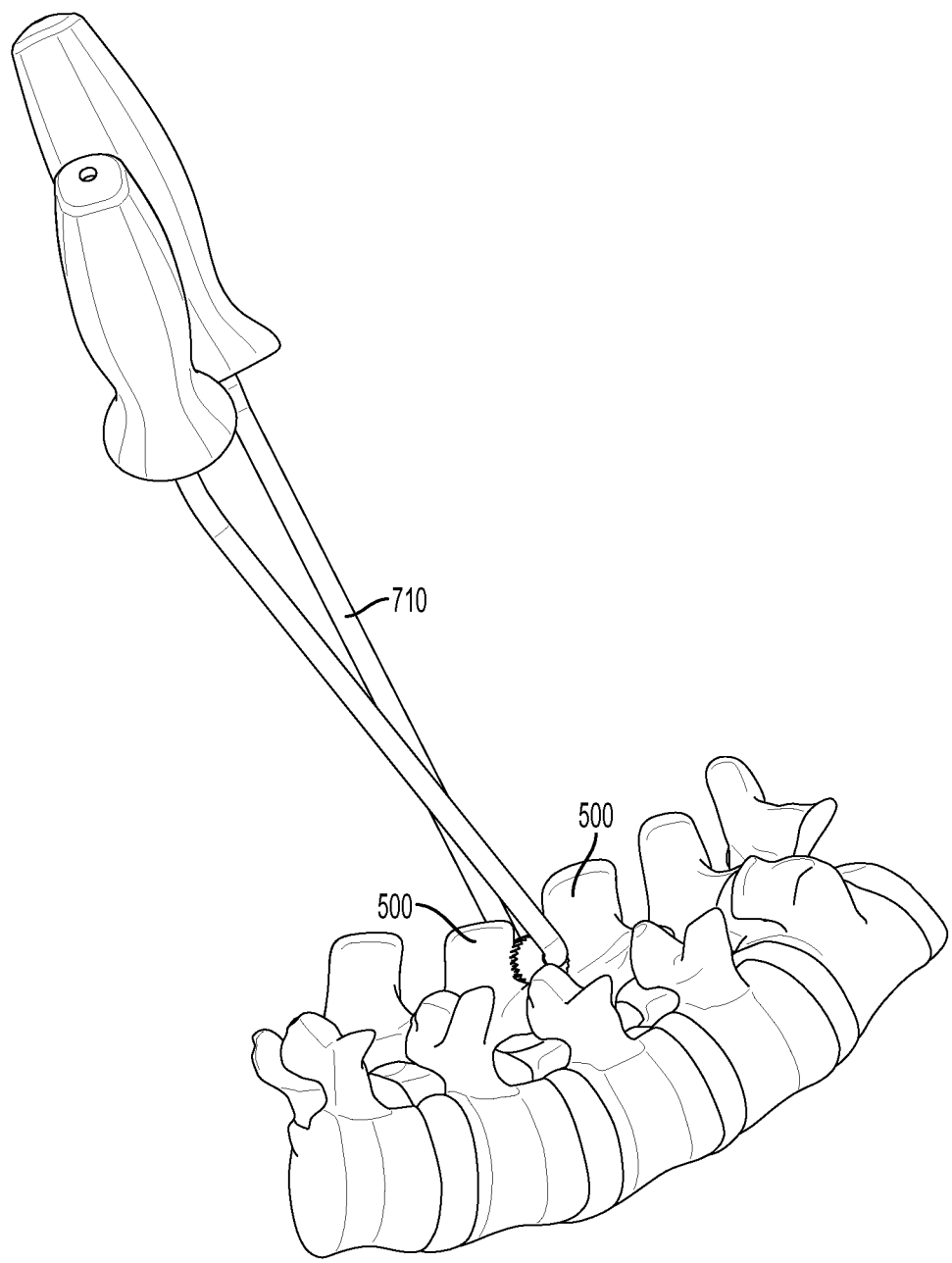
FIG. 29 is a perspective view of one aspect of an ISP fixation method, showing the step of using a rasp to prepare portions of the ISP space from a lateral approach.
Figure 30:
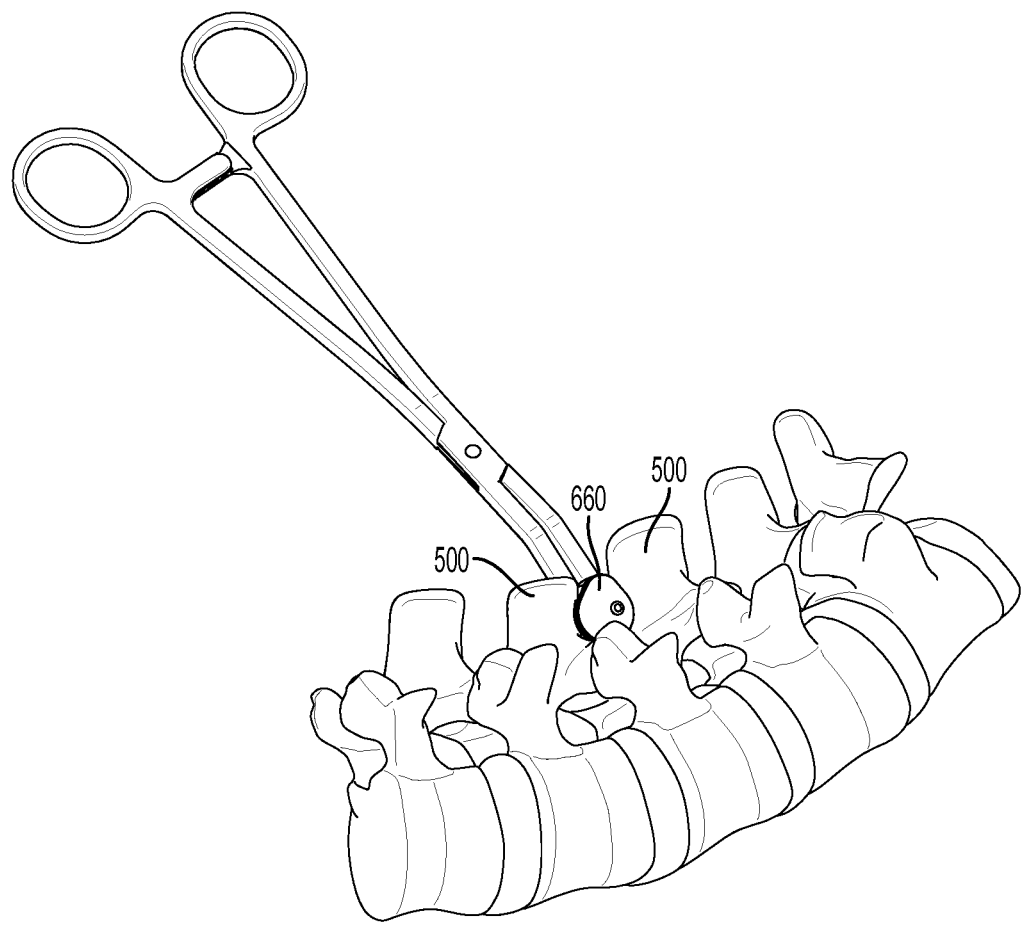
FIG. 30 is a perspective view of one aspect of a method of inserting an ISP fixation device where the cage is placed between two adjacent spinous processes from a lateral direction using an inserter.
Figure 31:
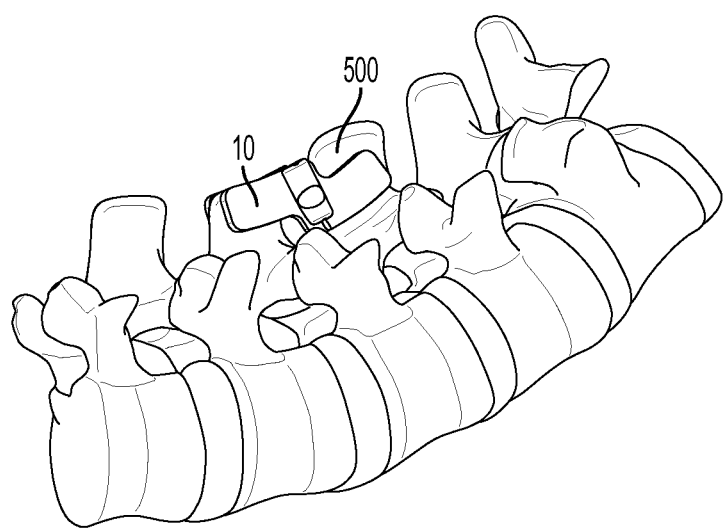
FIG. 31 is a perspective view of the final construct of an ISP fixation device in position using the method of FIG. 30.

In another aspect, a system for the fixation of spinous processes may comprise an inserter 660, first and second plates, a post, and a cage 400 as described above, where the cage defines a post bore therethrough. The inserter 660, in this aspect and as illustrated in FIG. 15, has a head 662 and an elongate shaft extending therefrom the proximal end 664 of the head 662. As can be seen, the head tapers toward its distal end 666. This system also comprises a tool to engage the elongate shaft 668 of the inserter, such as forceps, surgical pliers, and the like. In another aspect, a rasp 710, as shown in FIG. 29, can also be included.

Figure 24:
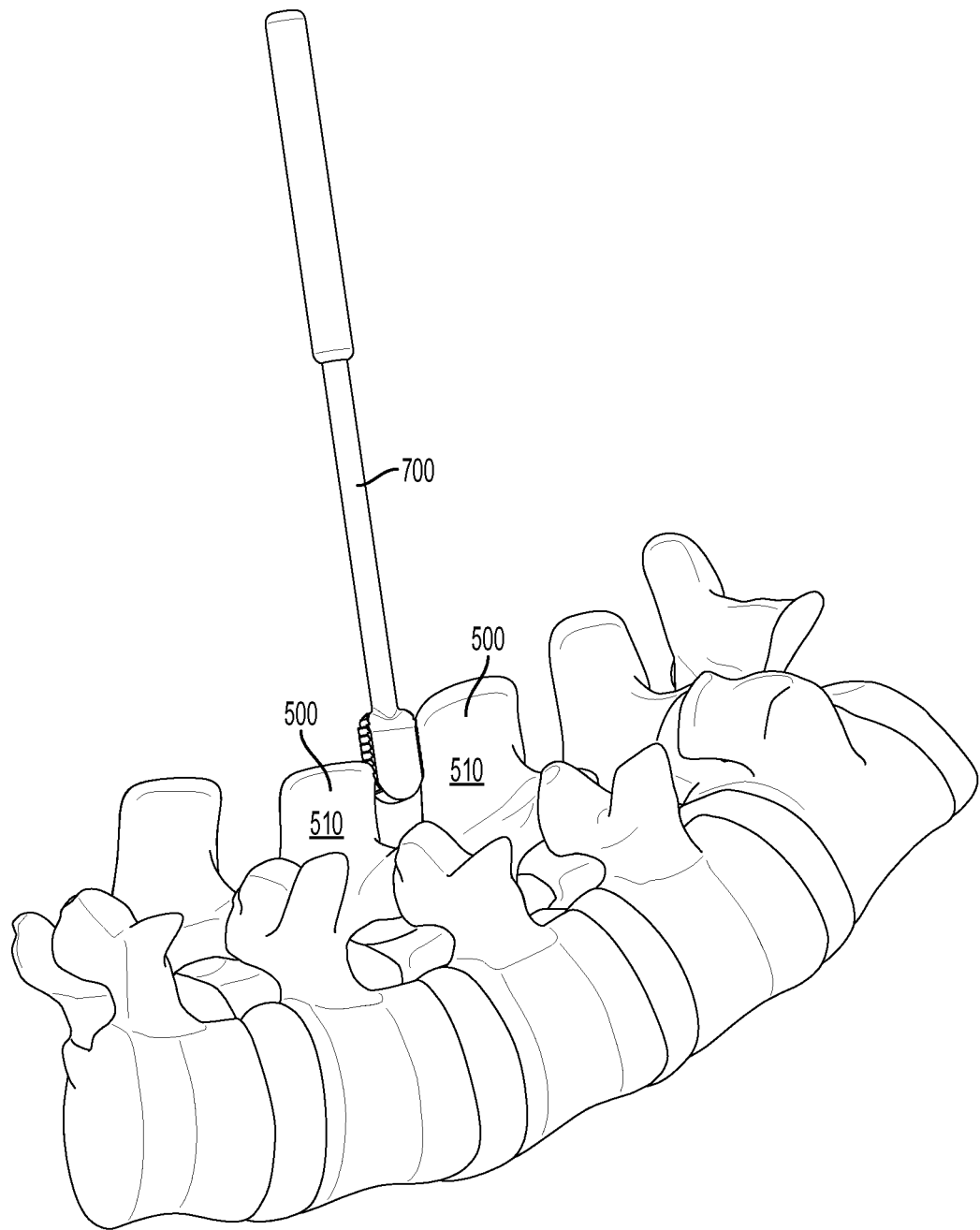
FIG. 24 is a perspective view of one aspect of an ISP fixation method, showing the step of using a rasp to prepare portions of the ISP space from a posterior-anterior direction.
Figure 25:
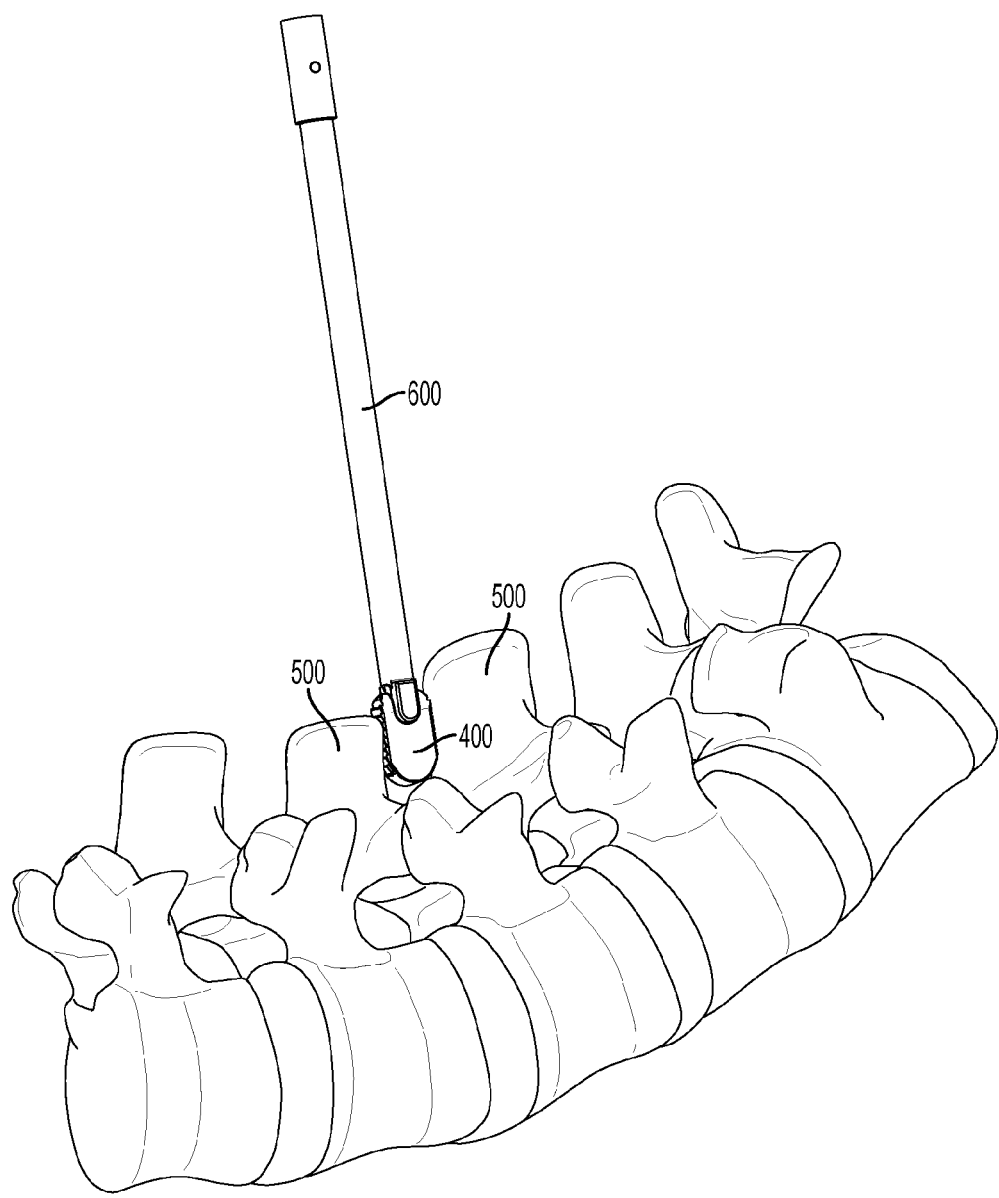
FIG. 25 is a perspective view of one aspect of an ISP fixation method, showing the step of inserting a cage between two adjacent spinous processes from a posterior-anterior direction.

A method of positioning a spinous process fixation system between first and second spaced spinous processes using a lateral approach and the system described above is also presented. In one aspect, the method comprises accessing an area substantially near the first and second spaced spinous processes. The surfaces of the adjacent spinous process can then be prepared. In one aspect, as shown in FIG. 24, a rasp is used to prepare the space. The cage is positioned onto the inserter 660 by positioning the elongate shaft 668 through the post bore. Using the forceps, for instance, the method comprises grasping the elongate shaft and urging the distal end 666 of the head 662 of the inserter laterally between the first and second spaced spinous processes until the cage is positioned therebetween the first and second spaced spinous processes. The inserter is then removed. The first plate is then positioned adjacent one side of the first and second spaced spinous processes, whereby the post is positioned therethrough the post bore. The second plate can then be positioned adjacent an opposite side of the first and second spaced spinous processes. Next, the method comprises compressing the first and second plates and affixing the second plate to the post, thereby maintaining the relationship between the first and second spaced plates.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A method of positioning a spinous process fixation system between first and second spaced spinous processes using a lateral approach, the method comprising:
   accessing an area substantially near the first and second spaced spinous processes;
   providing an implant comprising:
      a first plate having a post pivotally connected to and extending substantially therefrom a surface of the first plate;
      a second plate; and
      a cage having a leading end, a trailing end, a top portion, a bottom portion, and two opposed side portions defining a post bore therethrough;
   providing an inserter having a head and an elongate shaft extending therefrom a proximal end of the head, wherein the head tapers toward its distal end;
   positioning the cage onto the inserter by positioning the elongate shaft through the post bore:
   grasping the elongate shaft and urging the distal end of the head of the inserter laterally between the first and second spaced spinous processes until the cage is positioned therebetween the first and second spaced spinous processes;
   removing the inserter;
   positioning the first plate adjacent one side of the first and second spaced spinous processes, whereby the post is positioned therethrough the post bore;
   positioning the second plate adjacent an opposite side of the first and second spaced spinous processes; and
   compressing the first and second plates and affixing the second plate to the post, thereby maintaining the relationship between the first and second plates.

2. The method of claim 1, wherein the cage defines an interior cavity and wherein at least one of the top portion and the bottom portion of the cage defines a graft window in communication with the interior cavity.

3. The method of claim 1, wherein the first and second plates each have an upper portion and a lower portion, and wherein each upper portion has an upper portion longitudinal axis and each lower portion has a lower portion longitudinal axis.

4. The method of claim 3, wherein at least one of the upper portion longitudinal axes is substantially coaxially aligned with a respective lower portion longitudinal axis.

5. The method of claim 3, wherein at least one of the upper portion longitudinal axes is substantially parallel to a respective lower portion longitudinal axis.

6. The method of claim 1, wherein the second plate is spaced from the first plate and wherein the first and second spaced plates are substantially planar.

7. A method of positioning a spinous process fixation system between first and second spaced spinous processes using a lateral approach, the method comprising:
   accessing an area substantially near the first and second spaced spinous processes;
   providing an implant comprising:

a first plate having a post pivotally connected to and extending substantially therefrom a surface of the first plate;

a second plate spaced from the first plate; and a cage having a leading end, a trailing end, a top portion, a bottom portion, and two opposed side portions defining a post bore therethrough, wherein the leading end of the cage defines a substantially tapered nose, and wherein the trailing end of the cage defines a tool bore configured to engage a distal portion of an insertion tool;

urging the cage between the first and second spaced spinous processes from a lateral direction until the cage is positioned therebetween the first and second spaced spinous processes;

positioning the first plate adjacent one side of the first and second spaced spinous processes, whereby the post is positioned therethrough the post bore;

positioning the second plate adjacent an opposite side of the first and second spaced spinous processes; and compressing the first and second plates and affixing the second plate to the post, thereby maintaining the relationship between the first and second plates, wherein the cage is spaced therefrom each of the first and second spaced plates.

8. The method of claim 7, wherein the top portion of the cage is substantially concave when viewed from at least one of the leading end and the trailing end to substantially conform to the shape of at least one of the first and second spaced spinous processes.

9. The method of claim 8, wherein the bottom portion of the cage is substantially concave when viewed from at least one of the leading end and the trailing end to substantially conform to the shape of at least one of the first and second spaced spinous processes.

10. The method of claim 9, wherein the post of the first plate has a post length and a post diameter, and wherein the pivotable connection of the post to the first plate enables changing the attitude of the first plate relative to the second plate.

11. The method of claim 10, wherein the post is adjustably connected to the second plate to enable changing the spacing between the first plate and the second plate.

12. The method of claim 11, wherein and at least a portion of the post is configured to pass therethrough the post bore, wherein the post bore has a bore diameter that is larger than the post diameter and is sized to permit the post to move axially and radially within the post bore, thus permitting the cage to mate with the first and second spaced spinous processes substantially independent of the first and second spaced plates.

13. A method of positioning a spinous process fixation system between first and second spaced spinous processes using a lateral approach, the method comprising:

accessing an area substantially near the first and second spaced spinous processes;

providing an implant comprising:

a first plate having a post pivotally connected to and extending substantially therefrom a surface of the first plate;

a second plate, wherein the first plate has a surface facing a surface of the second plate and first portions of the facing surface of the first plate are in a first plane and first portions of the facing surface of the second plate are in a second plane, and wherein second portions of the facing surface of at least one of the first and second plates are flared away and lie in a plane that is angled with respect to the respective first and second plane such that, when the implant is implanted, at least one of the first plate and the second plate substantially conform to the shape of at least one of the first and second spaced spinous processes; and a cage having a leading end, a trailing end, a top portion, a bottom portion, and two opposed side portions defining a post bore therethrough;

urging the cage between the first and second spaced spinous processes from a lateral direction until the cage is positioned therebetween the first and second spaced spinous processes;

positioning the first plate adjacent one side of the first and second spaced spinous processes, whereby the post is positioned therethrough the post bore;

positioning the second plate adjacent an opposite side of the first and second spaced spinous processes; and compressing the first and second plates and affixing the second plate to the post, thereby maintaining the relationship between the first and second plates.

14. The method of claim 13, further comprising at least one first bone engaging spike protruding from at least a portion of at least one of the facing surfaces, wherein the at least one first bone engaging spike has a longitudinal axis.

15. The method of claim 13, wherein portions of at least one of the facing surfaces are recessed to accommodate the positioning of the cage.

16. The method of claim 14, further comprising at least one second bone engaging spike protruding from at least a portion of at least one of the facing surface, wherein the at least one second bone engaging spike has a longitudinal axis that is substantially parallel to the longitudinal axis of the at least one first bone engaging spike.

* * * * *